(12) United States Patent
Green et al.

(10) Patent No.: US 10,457,906 B2
(45) Date of Patent: Oct. 29, 2019

(54) METHOD FOR THE EFFECTIVE DELIVERY OF PHOTONIC ENERGY TO CULTURES IN A FLUID MEDIUM

(71) Applicant: Staterra LLC, Woodinville, WA (US)

(72) Inventors: Jared P. Green, Woolwine, VA (US); Eric R. Brooks, Woodinville, WA (US)

(73) Assignee: Staterra LLC, Woodinville, WA (US)

(*) Notice: Subject to any disclaimer, the term of this patent is extended or adjusted under 35 U.S.C. 154(b) by 374 days.

(21) Appl. No.: 14/686,279

(22) Filed: Apr. 14, 2015

(65) Prior Publication Data

US 2016/0068795 A1  Mar. 10, 2016

Related U.S. Application Data

(63) Continuation of application No. 13/921,037, filed on Jun. 18, 2013, now abandoned, which is a
(Continued)

(51) Int. Cl.
*C12M 1/00* (2006.01)

(52) U.S. Cl.
CPC ............ *C12M 31/06* (2013.01); *C12M 21/02* (2013.01); *C12M 31/08* (2013.01); *C12M 31/10* (2013.01); *C12M 39/00* (2013.01); *C12M 41/06* (2013.01)

(58) Field of Classification Search
CPC ...... C12M 31/06; C12M 21/02; C12M 31/08; C12M 39/00; C12M 41/06; C12M 31/10
(Continued)

(56) References Cited

U.S. PATENT DOCUMENTS

| 5,104,803 A | 4/1992 | Delente |
| 5,142,969 A * | 9/1992 | Chun ...................... A23B 4/12 |
| | | 435/289.1 |

(Continued)

FOREIGN PATENT DOCUMENTS

| SU | 1158573 A | 5/1895 |
| WO | 2008/135276 A2 | 11/2008 |
| WO | 2008/145719 A1 | 12/2008 |

OTHER PUBLICATIONS

Barbosa, "Microalgal photobioreactors: Scale-up and optimisation," *Doctoral Thesis, Wageningen University, The Netherlands*, 2003, 168 pages.

(Continued)

*Primary Examiner* — Liban M Hassan
(74) *Attorney, Agent, or Firm* — Seed Intellectual Property Law Group LLP

(57) ABSTRACT

An apparatus to prevent bio-filming during the delivery of photonic energy to a culture or set of organisms in a fluid culture medium, the device including a culture medium, a container configured to house the culture medium, and an assembly to generate and deliver a liquid energy transfer medium between the culture medium and the photonic device, the assembly including one or more apertures sized and shaped to form one or more liquid replenishing lenses and a fluid-light unit in the container to house the photonic device and the liquid energy transfer medium, the photonic device is at least one from among a photoreceptor, a photoemitter, or a combination of the photoreceptor and the photoemitter, and further including a pump coupled to the fluid-light unit, the assembly is configured to convey the photonic energy between the photonic device and the culture medium through the liquid energy transfer medium.

8 Claims, 15 Drawing Sheets

Related U.S. Application Data continuation of application No. 12/425,716, filed on Apr. 17, 2009, now Pat. No. 8,470,540.

(58) Field of Classification Search
 USPC .................................................. 435/292.1
 See application file for complete search history.

(56) References Cited

U.S. PATENT DOCUMENTS

| | | |
|---|---|---|
| 5,846,816 A | 12/1998 | Forth |
| 6,037,170 A | 3/2000 | Sekine |
| 6,069,113 A | 5/2000 | Kierzkowski et al. |
| 6,156,561 A | 12/2000 | Kodo et al. |
| 6,370,815 B1 | 4/2002 | Skill et al. |
| 6,602,703 B2 | 8/2003 | Dutil |
| 2005/0254055 A1 | 11/2005 | Peng |
| 2007/0050152 A1 | 3/2007 | Stevens et al. |
| 2007/0092962 A1 * | 4/2007 | Sheppard ............... C12M 21/02 435/266 |
| 2008/0311646 A1 | 12/2008 | Cong et al. |
| 2009/0029445 A1 | 1/2009 | Eckelberry et al. |
| 2009/0181438 A1 | 7/2009 | Sayre |
| 2009/0291485 A1 | 11/2009 | Shigematsu et al. |

OTHER PUBLICATIONS

Lee et al., "High-Density Algal Photobioreactors Using Light-Emitting Diodes," *Biotechnology & Bioengineering* 44(10):1161-1167, Nov. 20, 1994.

\* cited by examiner

METHOD FOR THE EFFECTIVE DELIVERY OF PHOTONIC ENERGY TO CULTURES IN A FLUID MEDIUM

BACKGROUND

Technical Field

The present disclosure relates to a method for the uniform distribution of photonic energy to a culture in a fluid medium that overcomes the problems of the turbidity of a dense culture and of bio-filming.

Description of the Related Art

The rapid and high density growth of photosynthetic microorganisms is critical in many industrial applications. These industrial applications include, without limitation, providing biomass used to extract biofuel, providing biomass used to produce methane by anaerobically digesting the biomass, producing food or specialized nutriceuticals, such as EPA and DHA for animals and humans, producing food and a growth environment for aquaculture, and consuming and sequestering industrial waste products such as $CO_2$. Providing faster growth and producing high density cultures is critical to achieving the operational scale necessary for current environmental and industrial needs. Ideally, improving the speed of growth and increasing the density of a culture will require less production space and consequently will lower the cost of associated facilities.

Effective Control of Light.

To maximize the growth of photosynthetic organisms, light must be available at the right intensity, the right frequency, and without excessive heat. Excessive light intensity can limit growth by inducing photo-respiration or bleaching the pigments needed for efficient cell growth. In addition, light intensity or light frequency in excess of the culture requirements may result in heat build-up that can limit culture growth. These problems are readily apparent in production systems that rely solely on direct solar light as a driver of photosynthesis, such as in ponds and raceways. Solar light is subject to extreme diurnal and seasonal variability. In addition, cultures relying on direct solar light are subject to periodic heating from light intensities and spectra not immediately useable by the culture.

The ability to effectively control light for 24 hours per day encourages faster growth of biomass and secondary metabolites as well as continuous consumption of $CO_2$. This results in a more efficient use of facilities, enabling a smaller footprint for a given level of production. However, the use of artificial light has a cost that must be minimized for successful industrial application.

Obstacles to Light Delivery.

The two major obstacles that reduce the uniform delivery of light to a culture are turbidity and biofilming. Turbidity occurs as a culture approaches a density where some of the organisms shade others from the light. Ensuring delivery of the appropriate amount of light to each organism becomes increasingly difficult as the density of the organisms in a culture increases. Turbidity within a culture results in some organisms receiving less light than they can use and non-productive absorption of light by other organisms. The absorption of excess light wastes energy and contributes to heat build-up.

Biofilming is an extremely widespread problem that occurs when a microorganism adheres to a surface. Most microorganisms, including species in all three domains, i.e., bacteria, eukaryotes, and archaea, perform processes that result in adhesion to surfaces and to other microorganisms. In industrial applications, biofilms often clog or corrode pipes and surfaces. In photobioreactors a biofilm can form over a light-delivery surface, thereby reducing the intensity and changing the spectra of the light transmitted.

Current techniques that address turbidity utilize tubular bioreactors that illuminate the culture as it flows through pipes of sufficiently narrow diameter. However, as the diameter of the pipes decrease, the friction and head pressure increase, requiring more powerful pumps to move the culture through the pipes. In addition, the large surface area of the pipe relative to the amount of culture exposed to the light increases the occurrence of biofilming. Some existing tubular systems periodically interrupt production and send pigs through the pipes to remove the biofilm from the interior surface of the pipe. Other systems include increasing the speed of flow and incorporating beads in the flow to increase turbulence and thus reduce biofilming. Increasing the speed of circulation requires longer pipes to insure that the culture is given sufficient light. All of these solutions increase the power required to maintain flow and thereby inflate the cost of production.

Another technique used to address turbidity in cultures includes exposing the culture to the light source as a shallow and wide flow. Generally in such systems biofilming is not a problem because no surface exists between the culture and the light source. However, the broadcasting of light over such a wide target prevents fine control of the intensity delivered and requires significant amounts of power to produce the required amount of light. The power cost is not a factor when direct solar radiation is used, but the process is subject to the variability entailed by solar radiation. When artificial light is used, the excess energy expenditure for the wide broadcast of light greatly increases the cost of production.

A third technique is described in Eckelberry et al., U.S. Patent Application No. 2009/0029445. The technique is to use a closed bioreactor, relying on an efficient source of artificial light, such as LEDs. The effects of turbidity are reduced by providing paddles that produce circulation. However, such a system is still subject to biofilming of the light sources.

The present disclosure addresses the costs added from use of artificial light by reducing the amount of light needed to maximize growth and preventing the obstruction of light sources by biofilming. Uniform and efficient distribution of light in the culture and the optimization of the spectra and intensity of light based on the particular organism being grown, the purpose of growing them, and their stage of growth helps to maximize growth of photosynthetic organisms.

BRIEF SUMMARY

The present disclosure is directed to delivering light to a culture by means of a flowing energy-transfer medium that prevents direct contact between a culture medium and a light delivery surface of a photonic energy source. The energy-transfer medium is illuminated by the source of photonic energy as it flows into the culture medium. As the energy-transfer medium flows into the culture medium, it breaks into many bubbles or drops and in the process provides surfaces that scatter light widely into the culture. This multiplicity of light paths and proximity of organisms to proximal light sources also decreases vulnerability to self-shading in a very dense culture. Bio-filming is prevented because the light delivery surface of the photonic energy source is isolated from direct contact with the culture. The energy-transfer medium flowing into the culture medium acts as a series of lenses that continually replenish themselves as a consequence of the flow and therefore are not subject to bio-filming.

In one embodiment, the method includes preventing bio-filming and overcoming turbidity during the delivery of photonic energy to a culture or set of organisms in a fluid culture medium. The method includes distributing photonic energy into the fluid culture medium via a fluid energy-transfer medium. The fluid energy-transfer medium may be at least one of a gas and a liquid. The distributing of the photonic energy includes introducing the photonic energy from a first location to the fluid culture medium and introducing the energy-transfer medium from at least one second location spaced away from the first location to the fluid culture medium. The photonic energy is distributed into the culture medium via the energy-transfer medium that is introduced from any location by at least one from among transmission, reflection, refraction, and diffraction. Ideally, the photonic energy is produced using a source of photonic energy that is separated from the culture medium by the energy-transfer medium.

In one embodiment of the present disclosure, a method of preventing bio-filming during the delivery of light to a culture or set of organisms in a fluid culture medium is provided. The method includes introducing a fluid energy-transfer medium into the culture medium through an interface and distributing light into the fluid energy-transfer medium as it is introduced into the culture medium. The method further includes producing the light using a source of light that is separated from the culture medium by at least one from among the interface, the energy-transfer medium, and a combination of the interface and the energy-transfer medium. The light source includes at least one from among artificial light, solar light, and a combination of artificial light and solar light. In addition, producing the light locally at the interface may be accomplished by a controllable artificial light source that includes at least one from among a solid-state source, a gas-discharge source, and an incandescent source. The method also includes delivering locally produced or remotely captured light to the interface by at least one from among a fiber optic medium, a light pipe, and a waveguide.

The method further includes adjusting a spectral content of the light source, the adjusting determined by at least one from among, phototrophic needs of the culture, wasted energy of producing particular light frequencies, and impact of specific light frequencies on an environment adapted to growing phototrophic organisms. The adjusting of the spectral content of the light source may include at least one from among, selecting the light source for the spectral content, combining a plurality of selected light sources to produce a target spectral content, filtering the light source, shifting wavelengths of the light source, and electronic control of the light source.

In addition, the adjusting the spectral content of the light source may include isolating specific light frequencies to a first set of frequencies, with at least one second set containing a portion of remaining light frequencies and delivering the first set of frequencies to the culture medium, and at least one second set of frequencies to at least one other process. In another embodiment, the method includes providing an array of light sources having a plurality of light sources configured to provide specific light frequencies and adjusting the spectral content of the light sources by selectively controlling the light sources in the array of light sources.

In yet another embodiment of the present disclosure, the method includes introducing a gaseous or liquid nutrient into the fluid energy-transfer medium. The rate of introduction of the fluid energy-transfer medium is adjustable to optimize the delivery of photonic energy to the culture medium, and the adjusting is determined by phototrophic needs of the culture.

Alternatively, the method adjusts a size or shape, or both the size and shape, of an aperture of the interface to optimize the delivery of photonic energy to the culture medium, the adjusting determined by at least one from among viscosity, turbidity, shape, and size of an environment and phototrophic needs of target species in the culture medium. The environment may be adapted to grow phototrophic organisms. In addition, properties of the energy-transfer medium include at least one from among a refractive index, a specific gravity, a surface tension, a viscosity, a transmitivity, a reflection loss, and an absorption coefficient to enhance coupling of photonic energy from the light source to the culture. The energy-transfer medium may be continually introduced to allow measurement of parameters of the culture.

The method also includes controlling a rate of introduction of the energy-transfer medium into the culture. The rate of introduction of the energy-transfer medium can be static for a selected or predetermined period of time.

In another embodiment of the present disclosure, a process for providing photonic energy to a culture medium includes injecting a fluid energy-transfer medium into the culture medium from a fluid delivery unit and transmitting photonic energy to the culture medium from a photonic energy delivery device through the fluid energy-transfer medium. Preferably, the culture medium is separated from a photonic energy source in the photonic energy delivery device by means of the fluid energy-transfer medium.

In accordance with yet another embodiment of the present disclosure, a method is provided that includes forcing a nutrient enriched energy-transfer fluid into a culture medium; providing light from a light source through the nutrient enriched energy-transfer fluid into the culture medium; and using the nutrient enriched energy-transfer fluid to separate the light source from the culture medium. Ideally, providing light from the light source includes using a photonic energy source that provides light chosen from the group consisting of artificial light, solar light, and a combination of artificial light and solar light.

In yet another embodiment, a method of preventing bio-filming during a transfer of photonic energy between a photonic device and a fluid culture medium is provided. The method includes introducing a fluid energy-transfer medium into the fluid culture medium through an interface and transmitting photonic energy through the fluid energy-transfer medium as the fluid energy-transfer medium is introduced into the fluid culture medium. In addition, the method may include receiving photonic energy at the photonic device from the culture medium through the energy-transfer medium. The method may also include receiving photonic energy in the culture medium from the photonic device.

The method also includes receiving photonic energy at the photonic device from the culture medium through the energy-transfer medium and receiving photonic energy in the culture medium from the photonic device. Ideally, the photonic device is separated from the culture medium by at least one from among the interface, the energy-transfer medium, and a combination of the interface and the energy-transfer medium. Additionally, a culture or a set of organisms in the culture medium transmit photonic energy through the energy-transfer medium by at least one from among transmission, reflection, refraction, diffraction, and luminescence.

The photonic device may be at least one from among a photoreceptor, a photoemitter, a combination of the photoreceptor and the photoemitter, a lens, and a waveguide. Additionally, the photonic device may be a photometric instrument to measure at least one from among a spectrum, an intensity, a reflection, a refraction, a diffraction, an absorption coefficient, a transmission coefficient, a wavelength shift, a time duration, an amount of radiant energy, and a luminescence.

The method may include altering properties of the energy-transfer medium to include at least one from among a refractive index, a specific gravity, a surface tension, a viscosity, a transmittivity, a reflection loss, and an absorption coefficient to enhance coupling of photonic energy between the photonic device and the culture medium. In addition, the energy-transfer medium may be continually introduced to allow the photonic device to measure without biofilming at least one from among a culture parameter, a culture medium parameter, a culture growth environment parameter, and a process control parameter. The photonic device may also provide photonic energy for the phototrophic needs of a set of organisms or a culture in the culture medium.

In yet another embodiment, spectral control of the light source may be achieved by filtering or isolating selected frequencies of solar light so that it may contain only the wavelengths that can be absorbed by the target organisms. The frequencies of light that are not useful to the target organisms may be directed to other processes such as conversion to electrical energy by photovoltaic cells or production of mechanical energy from a heat engine.

The filtered or isolated solar energy may be combined with an artificial light source to provide a 24-hour light source. The filtered solar light may be captured remotely and delivered to the growth environment through a wave guide while sunlight is available. To improve efficiency, the artificial light source may have a spectral content control and may be produced locally to the growth environment.

As will be appreciated from the foregoing summary, the disclosed embodiments provide a method for the efficient delivery of light to a highly turbid dense culture in a fluid medium that overcomes the problems of bio-filming of the light source and uneven distribution of light to cultures in the culture medium. Light is less likely to be reflected back at the source or converted into waste heat when evenly distributed by the mechanisms of transmission, reflection, refraction, and diffraction available from a distribution array created by a flowing energy-transfer medium. Shielding the original light source with a fluid energy-transfer medium prevents the light source from coming in contact with the culture, and is thus not subject to bio-filming. Additionally, light delivered by this method allows fine control of spectra and intensity, reducing energy cost by only producing and delivering photonic energy productive to growth of the target organism.

The novel system for light delivery described herein provides very close control of the light delivered. The system reduces the cost of artificial light and allows the optimization of the spectral content of the light for organism growth.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

Figure 1:
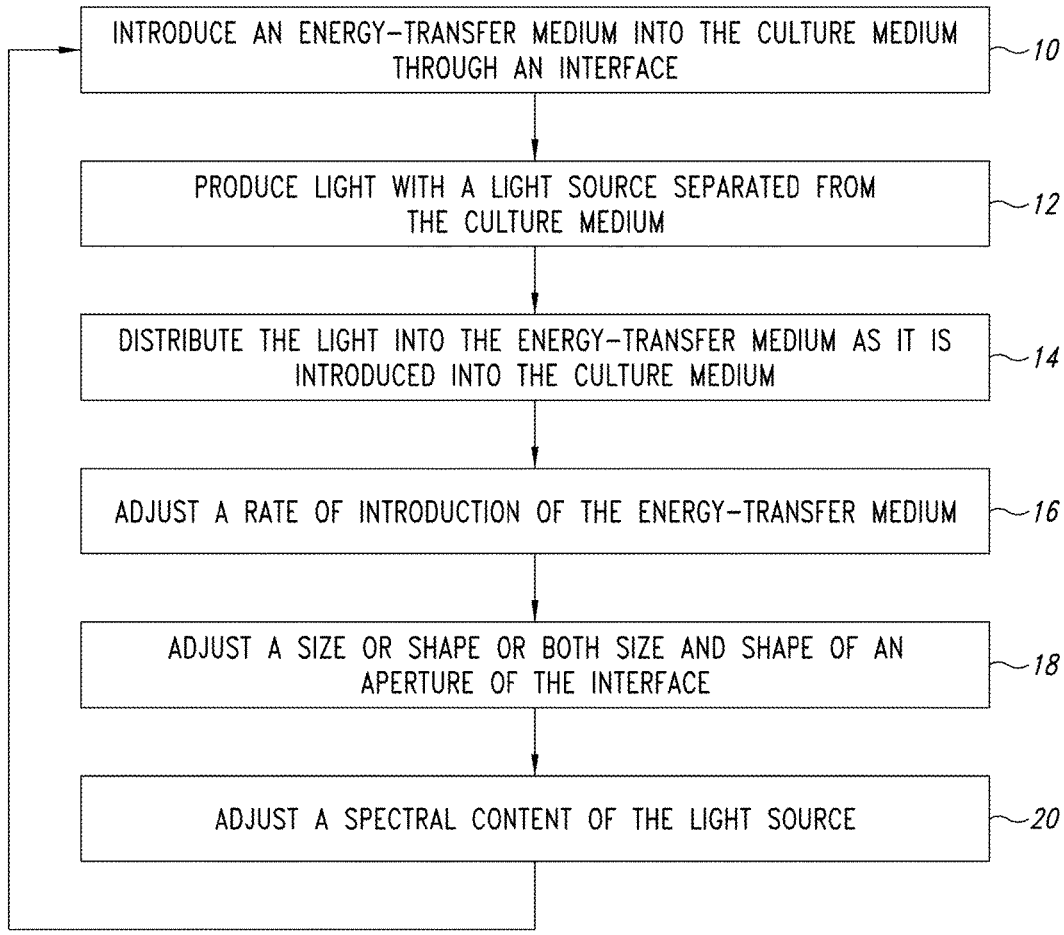
FIG. 1 is a flowchart of the process of delivering photonic energy to a culture without bio-filming of the light source.

In the following description, certain specific details are set forth in order to provide a thorough understanding of various embodiments of the disclosure. However, one skilled in the art will understand that the disclosure may be practiced without these specific details. In other instances, well-known structures associated with the containing, conveying, storing, and transporting of cultures as well as generating and conveying light energy have not been described in detail to avoid unnecessarily obscuring the descriptions of the embodiments of the present disclosure.

Unless the context requires otherwise, throughout the specification and claims that follow, the word "comprise" and variations thereof, such as "comprises" and "comprising," are to be construed in an open, inclusive sense, that is, as "including, but not limited to." Unless the context requires otherwise, throughout this specification and the claims that follow, the words "light" and "photonic energy" and variations thereof, are to be construed as interchangeable.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the drawings, identical reference numbers identify similar features or elements. The size and relative positions of features in the drawings are not necessarily drawn to scale. For example, the shapes of various features are not drawn to scale, and some of these features are arbitrarily enlarged and positioned to improve drawing legibility.

One general embodiment of the present disclosure is an energy-transfer medium that consists of a gas, ideally a mixture of CO2, which acts as a nutrient for photosynthetic cultures, and filtered air. Photonic energy is provided by a selected array of LEDs. The environment into which this gas mixture flows is a bioreactor that uses a fluid culture medium, an independent means of circulation, and that is adapted to growing photosynthetic organisms. However, it is to be understood that the energy-transfer medium could consist of a liquid. In addition, nutrients in the energy-transfer medium could either be omitted or delivered as a liquid fertilizer. The environment into which the energy-transfer medium flows could be a pond or a raceway that is adapted to growing photosynthetic organisms. In addition, a method of light delivery is provided. It is expected to operate in the environment that provides the other essentials for culture growth.

Further, the method of delivering photonic energy into the culture by means of a flowing energy-transfer medium is independent of the source of photonic energy. This energy could be provided by artificial light generated locally, i.e., near the point of entry through an interface into the culture medium, or by a remotely located light source and transmitted to the interface by one or more of a fiber optic medium, a light pipe, or a waveguide. "Artificial light" is here defined as photonic energy that is generated by a controllable light source that includes at least one from among solid state lighting (including LED and electroluminescent technology), gas discharge lamps (including metal halide and florescent), and incandescent light. Light generated remotely may include solar radiation, artificial light, or a combination of solar radiation and artificial light.

Regardless of the source of photonic energy, the method disclosed herein delivers the photonic energy into the culture medium using the flowing energy-transfer medium, thereby avoiding the problems of biofilming and of self shading from the high turbidity provided by other organisms.

While LED's are a preferred source of artificial light, it is to be understood that the method of the present disclosure can be implemented with all forms of light. Turning first to FIG. 1, shown therein is a sequence of operations in accordance with one method of the present disclosure. Various implementations of the energy-delivery method and apparatus are next described, which are selected as non-exclusive examples of the variety of forms of this method of light delivery.

In a first embodiment a "passive aperture" system is operated in a very simple bioreactor, while in a second embodiment an "optimized energy-transfer medium" optimizes the coupling properties of the energy-transfer medium to provide efficient light delivery. A third "flow control" embodiment uses flow regulators to optimize the delivery of the energy-transfer medium into the fluid culture. The fourth "spectral control" embodiment controls the photonic spectra of the light in order to conserve energy costs and to adapt the system to the needs of different microorganisms, and in a fifth "instrumentation aperture" embodiment the flowing energy-transfer medium is used to protect operative parts of an optical measurement instrumentation, which monitors and controls the delivery of light. A sixth "distribution array" embodiment optimizes one energy-transfer medium as a transmission conduit for coupling light into the culture medium and a different energy-transfer medium as a distribution array for light that has already entered the culture medium. In each of these embodiments, the flowing energy-transfer medium is used to more effectively deliver photonic energy to cultures in the culture medium.

Referring initially to FIG. 1, a general overview of one process in accordance with the present disclosure is illustrated. In block 10, the process includes introducing an energy-transfer medium into a culture medium through an interface. The energy-transfer medium may be fluid and is continually introduced into the culture medium. Nutrients, in liquid or gaseous form, can be provided to the culture medium by way of the energy-transfer medium. The culture medium is in this embodiment a growth environment for photosynthetic organisms that include algae and cyanobacteria.

In block 12, the process includes providing light from a light source, which is separated from the culture medium by the energy-transfer medium to prevent bio-filming of the light source. The culture medium can be separated from the photonic energy source by the interface, the energy-transfer medium, or a combination of both the interface and the energy-transfer medium.

Ideally, the photonic energy source provides light from a local artificial light source such as an LED, another solid-state source, a gas-discharge source, or an incandescent source or any combination of the foregoing. Preferably, the light source is controllable. However, the photonic energy source is also adapted to emit remotely captured photonic energy such as solar light or a combination of artificial and solar light. Remotely captured photonic energy is transported by a fiber optic medium, a light pipe, or a waveguide.

In block 14, the light is distributed into the energy-transfer medium simultaneous with introducing the energy-transfer medium into the culture medium. The properties of the energy-transfer medium are selected from at least one from among a refractive index, a specific gravity, a surface tension, a viscosity, a transmittivity, a reflection loss, and an absorption coefficient to enhance delivery of photonic energy from the light source to the culture medium.

In one embodiment, the energy-transfer medium is introduced into the culture medium without having been previously illuminated. The bubbles thus formed then can scatter light introduced through a different aperture that is protected by flowing energy-transfer medium or introduced from some other source. In block 16, a rate of introduction of the energy-transfer medium is adjusted to optimize the delivery of photonic energy to the culture medium. The rate of adjustment depends on the phototrophic needs of the culture and on the relative percentages of nutrients in the energy-transfer medium. The energy-transfer medium is introduced continually to allow for measurements of certain parameters of the culture. In one embodiment, the energy-transfer medium is static for a predetermined or selective period of time to optically detect characteristics of the culture. Minimizing the period of time the energy-transfer medium is not flowing prevents bio-filming of the photonic energy source.

In the next step illustrated in block 18, the process optionally provides for adjusting a size or shape or both size and shape of the aperture of the interface to optimize delivery of photonic energy to the culture medium. Factors evaluated in determining the amount of adjustment include viscosity, turbidity, rate of movement of the culture medium, shape and size of the environment, and phototrophic needs of target species in the culture medium. The process illustrated in FIG. 1 is executed in an environment that is otherwise adapted to growing phototrophic organisms.

In the next step illustrated in block 20, the process optionally provides for adjusting a spectral content of the light source. The adjustments may include selecting the light source for a particular spectral content, combining a plurality of selected light sources to produce a target spectral content, filtering the light source, and electronic control of the light source. In addition, the adjustments may be made to optimize the spectral content directed to phototrophic needs of the culture, separate utilization of the wasted energy of producing particular light frequencies, and impact of specific light frequencies on an environment adapted to growing phototrophic organisms.

Figure 2:
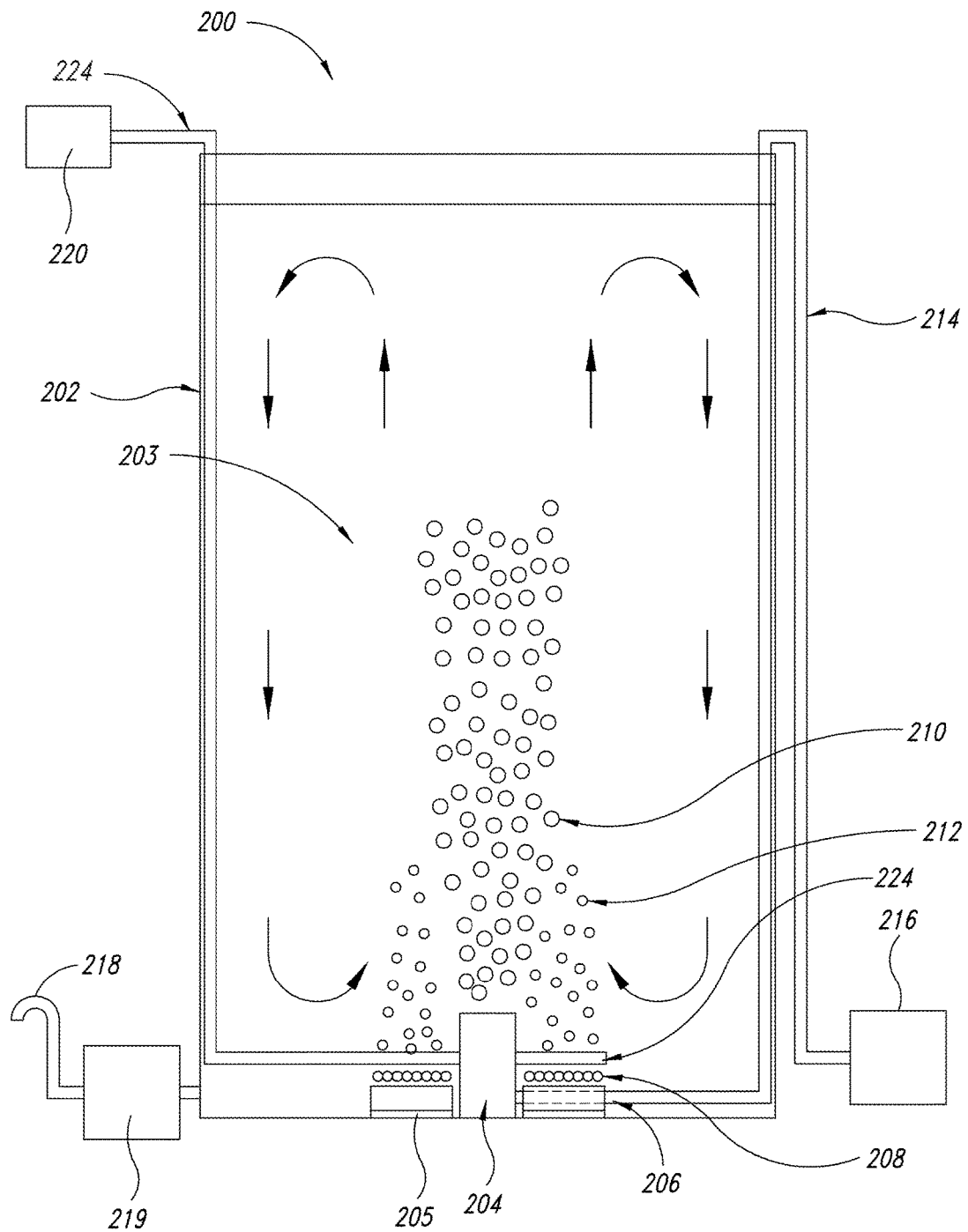
FIG. 2 is a cross-sectional side view of a system for delivery and distribution of light to a culture, according to one embodiment of the present disclosure.

In the "passive aperture" embodiment of a light delivery system 200, the following general description and more specific description that follow are presented in conjunction with FIGS. 2-7A. FIG. 2 illustrates the representative light delivery system 200 that carries out the general method described above. A bioreactor 202 provides a production space 203 adapted to contain the culture medium and to efficiently distribute photonic energy through the culture medium in the production space 203. Enclosed in or attached to the bioreactor 202 are at least one fluid-light unit 206 and an air-lift unit 204. The interface plate 208 is sized and shaped to attach to the fluid-light unit 206 and to separate the contents of the fluid-light unit 206 from the culture medium. An air-tight seal between the interface plate 208 and the fluid-light unit 206 avoids releasing the energy-transfer medium and photonic energy from places other than the holes 222 in the interface plate 208.

The interface plate 208 attaches to the fluid-light unit 206. In one embodiment, the interface plate 208 is a 3/16 inch thick Plexiglas plate into which 108 evenly spaced holes 222 of 1/16 inch diameter are drilled. Other materials, such as metal and other plastics, can be used for the interface plate 208. These holes allow the energy-transfer medium, in this case the air/$CO_2$ mixture, to flow, under the 7 psi pressure, into the culture medium. This injection of the energy-transfer medium prevents the culture from coming into contact with the photonic energy source 205 in the fluid-light unit 206, thus preventing biofilming of the photonic energy source 205. In one embodiment, the interface plate 208 may be formed as an integral component of the fluid-light unit 206 or as a separate component. Alternatively or additionally, the fluid-light units 206 may be manufactured as fixed components of the bioreactor 202.

Figure 3:
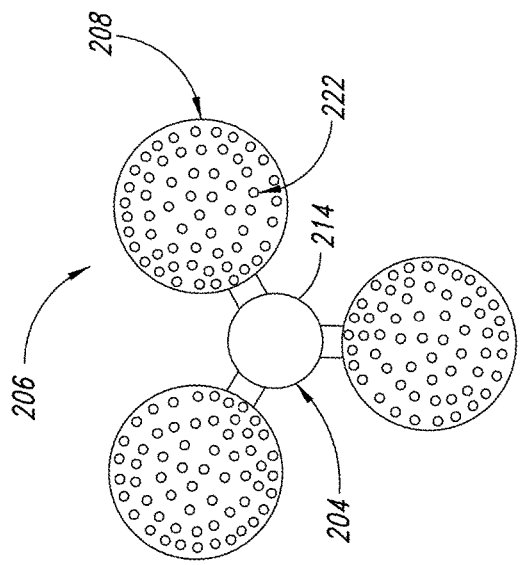
FIG. 3 is a top view of a plurality of fluid-light units, according to another embodiment of the present disclosure.

FIG. 3 illustrates a top view of three fluid-light units 206 spaced around the air-lift unit 204, which may be placed or securely attached to a bottom of the bioreactor 202. The number and arrangement of fluid-light units 206 may be varied to meet the needs of the culture medium and the size of the bioreactor 202. In some embodiments, the air-lift unit 204 may be omitted.

Figure 4:
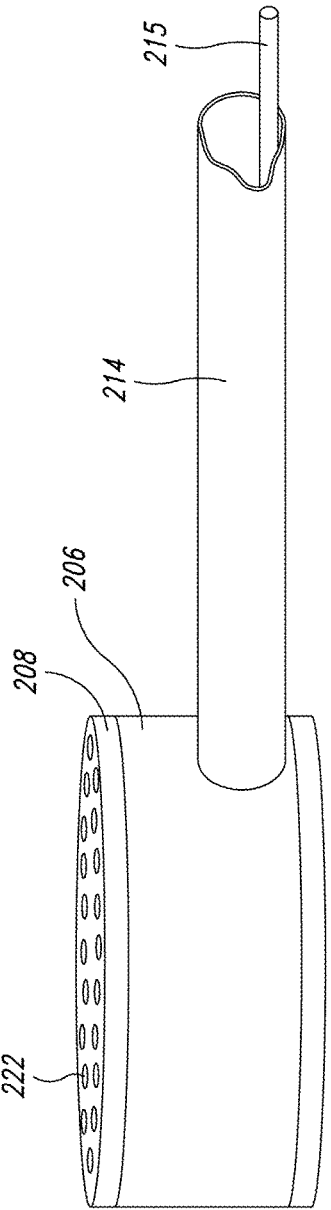
FIG. 4 is an enlarged isometric view of a fluid-light unit from FIG. 3.

FIG. 4 illustrates one embodiment of the fluid-light unit 206. Preferably, each fluid-light unit 206 is a weighted, 5 inch diameter pot into which a mixture of the nutrient gas and filtered ambient air, i.e., the energy-transfer medium is pumped through flexible piping 214. Pump 216 propels the mixture into the fluid-light unit 206 through flexible piping 214 (see FIG. 2). A flexible conduit 215 may pass through the flexible piping 214 to couple electrical components incorporated in the fluid-light unit 206 with controllers or power sources external to the production space 203, such as a process controller 230 in FIG. 6. The flexible conduit 215 may isolate conductive connectors from the energy transfer medium. In another embodiment, the flexible conduit 215 may be a light pipe that provides the photonic energy to the fluid-light unit 206.

Figure 5:
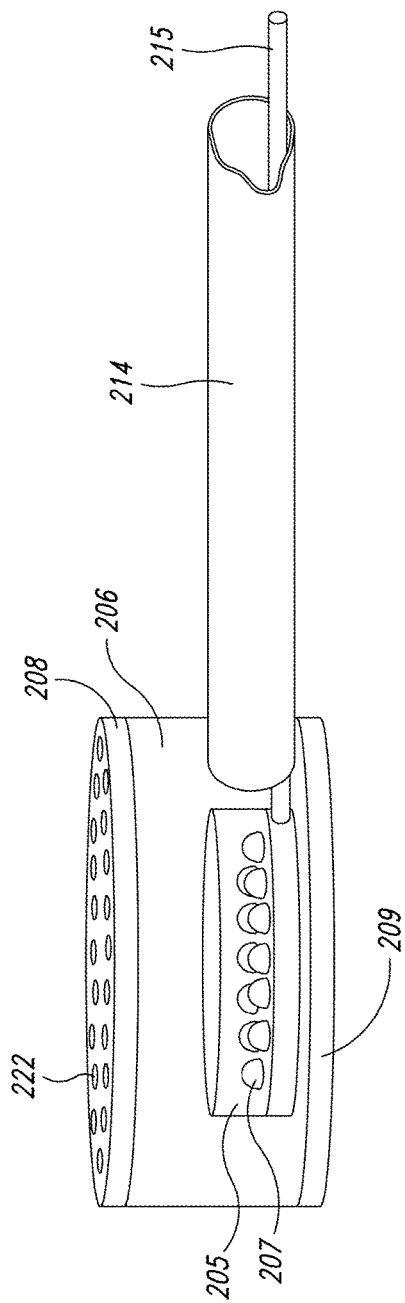
FIG. 5 is an enlarged isometric view of another embodiment showing a localized light source in the fluid-light unit of FIG. 4.

In the cultivation of some microorganisms, the energy-transfer medium may include $CO_2$, $N_2$ or, $NH_3$. In one embodiment, the pressure of this gas mixture is maintained at 7 psi with a concentration of $CO_2$ at or below 5%. This concentration maintains a pH level between 8 and 9, which is acceptable to most commercially grown green and golden algae. A higher level of $CO_2$ (pH 10) would be acceptable for cyanobacteria, such as *spirulina platensis*. The air may be filtered before introduction into the fluid-light unit 206 by a 5 μm resin cartridge filter or a spun or pleated filter FIG. 5 shows an array of LED lamps 207 that may be used as the photonic energy source 205 to produce a total of 10 watts of energy within the fluid-light unit 206. The photonic energy source 205 is incorporated with the fluid-light unit 206 and the interface plate 208 and may be securely attached to a base 209 of the fluid-light unit 206 to prevent movement. The conduit 215 may couple the LEDs 207 to a power supply or control circuitry (not shown). These LED lamps 207 are selected to produce light in the regions of the spectrum critical for growth of the target culture.

Figure 6:
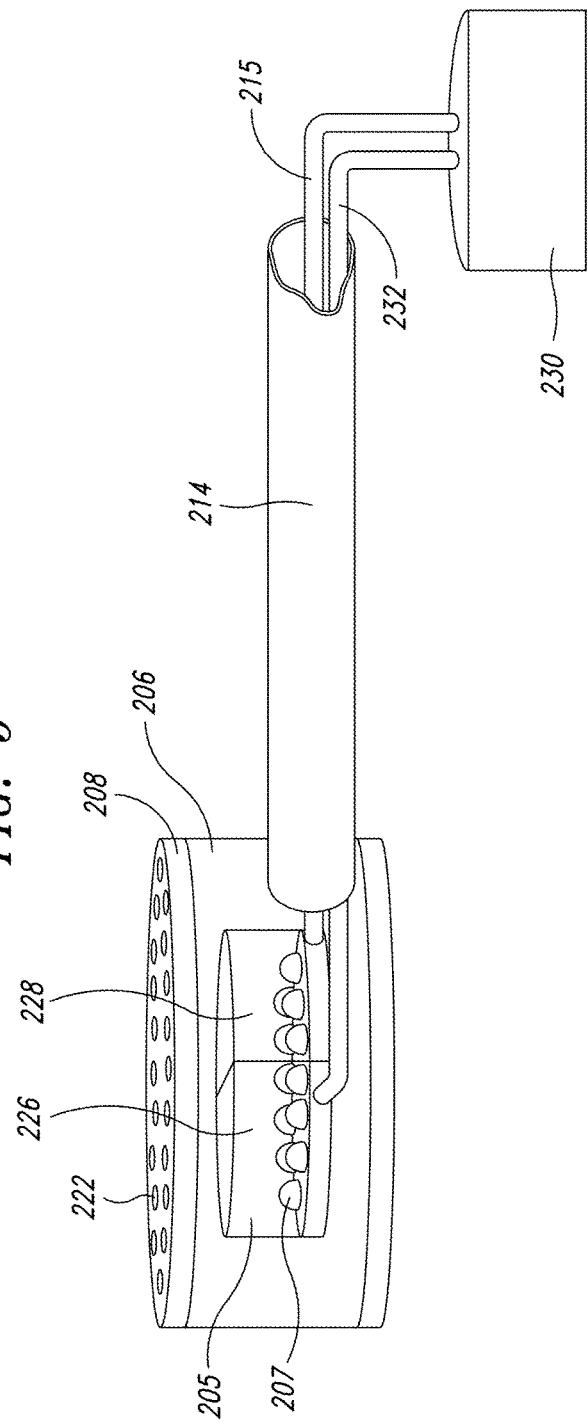
FIG. 6 is an enlarged isometric view of yet another embodiment showing a localized light source with controlled spectrum in the fluid-light unit of FIG. 4.

As illustrated in FIG. 6, the photonic energy source 205 may include more than one type of array of LEDs 207 to optimize the spectrum of light for the particular culture. For example, the photonic energy source 205 may have a red light source 226 and a blue light source 228. The flexible conduit 215 couples the process controller 230 to the blue light source 228. A second flexible conduit 232 couples the process controller 230 to the red light source 226.

For many commercially produced organisms the critical spectrums include red, centered on 680 nm, and blue, centered on 465 nm. For maximizing biomass growth, a 2:1 ratio of blue to red light is acceptable. If the production objective were to increase lipid content, then a higher proportion of red light could be used. The selective spectrum saves energy cost and prevents non-productive spectra from causing potentially harmful heating of the culture. Other colors and spectra of light may be generated by the light sources 226, 228 depending on the needs of the culture medium.

Figure 7:
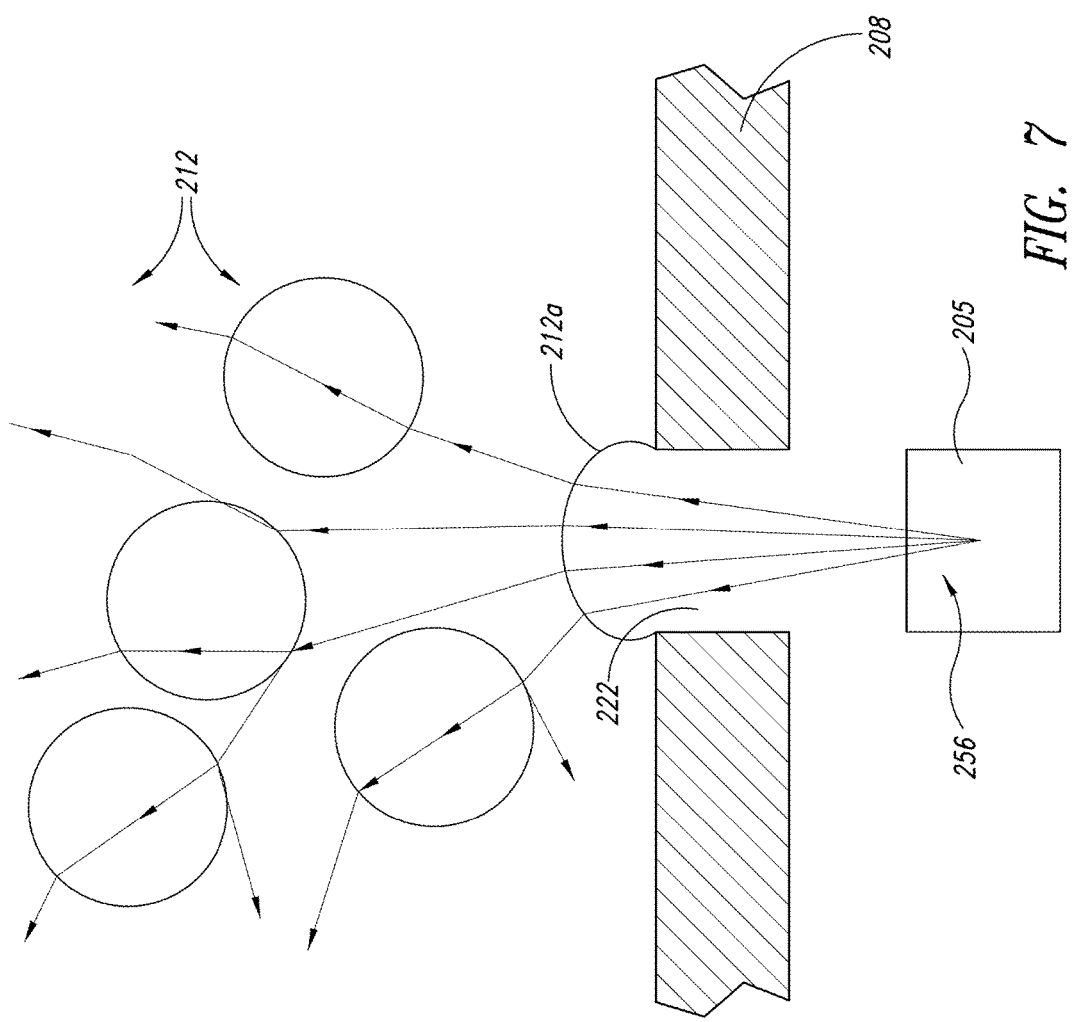
FIGS. 7 and 7A are enlarged cross-sectional views of apertures through an interface plate, according to one embodiment of the present disclosure.

FIG. 7 shows how bubbles 212 form in the individual aperture or hole 222 formed in the interface plate 208 and transmit, reflect, refract, diffract, and otherwise scatter light from the photonic energy source 205 into the culture medium. The fluid-light unit 206 and the photonic energy source 205 deliver light to the culture medium. As the energy-transfer medium enters the fluid culture medium it creates a rising column of bubbles 212 (see FIG. 2). The bubbles 212a, when they are still in the aperture or hole 222, act as lenses that are frequently replenished and reflect and refract light as shown by a plurality of light rays 256. The light rays 256 originate at the photonic energy source 205 and travel through the energy-transfer medium as the energy-transfer medium forms an individual bubble 212a. The bubble 212a acts as a boundary between the photonic energy source 205 and the culture medium. The continuous formation of the bubbles 212a prevents biofilming of the photonic energy source 205. The boundary that the bubble 212a creates assists in distributing the light rays 256 because of the different refractive indices of the energy-transfer medium and the culture.

The bubbles 212 are advantageous because they scatter light into the culture from many directions by transmission, reflection, refraction, and diffraction and release photonic energy in close proximity to a large number of the organisms in the culture. Together with circulation 210 provided in the culture environment, this greatly increases the proportion of cells that are exposed to photonic energy and therefore decreases the effect of turbidity without requiring the energy-inefficient circulation impediment that is inherent to a tubular bioreactor.

Figure 7A:
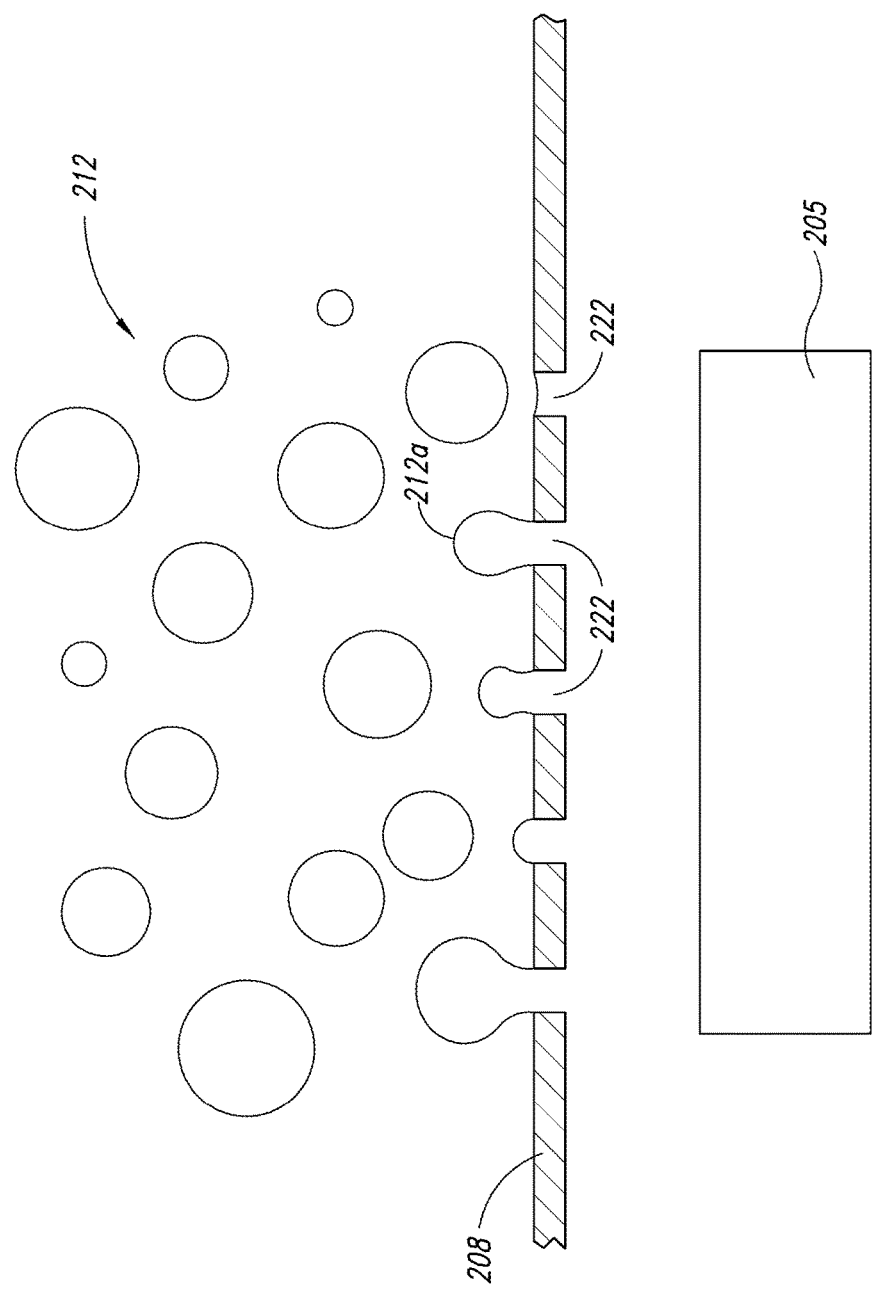

FIG. 7A further illustrates the formation of bubbles 212a through the interface plate 208. The bubbles 212a are shaped by the interface plate 208 that has the plurality of evenly spaced apertures or holes 222 sized to ensure that bubbles 212 emerging into the culture medium are not so small as to cause cell destruction from cavitation. As the energy-transfer medium is injected from the fluid-light unit 206 into the culture medium the bubbles 212 are in gaseous or droplet form. Each bubble 212a acts as a replenishing lens for providing photonic energy to the culture medium. As each bubble 212a forms a new replenishing lens forms so that the culture is continuously provided with energy from the photonic energy source 205.

The sizes of the holes 222 in the interface plate 208 are essential to the formation of bubbles 212 with an optimal shape. Bubbles 212 formed from an under-sized aperture can produce turbulence (mainly inertial cavitation) that can destroy up to 20% of the organisms in the culture. Inertial cavitation is the process where a void or a bubble in a fluid medium rapidly collapses due to a lower vapor pressure and then rapidly re-expands. The collapse of the bubbles and subsequent explosion produces a local shock wave that can tear cell walls.

The destructive effect of cavitation suggests that roughness or sharp edges along aperture walls are to be avoided. In one embodiment, $1/16$ inch holes 222 produce bubbles 212 up to one inch in diameter and avoid cell destruction by cavitation. Larger bubbles 212 can be used, but are empirically less efficient at evenly distributing light. Because of the barrier provided by the energy-transfer medium, no part of the culture medium is in contact with or exposed to the source of photonic energy 205. The size and rate of emission of the bubbles 212 and 212a are adjustable according to the optimal photonic energy delivery, the viscosity, the turbidity, and the characteristics of the organism grown in the culture medium.

Ideally, light will be generated locally by LEDs 207. LED technology currently offers some of the highest electric to photonic energy conversion efficiency available, with an added advantage of concentrating photonic energy production in a narrow spectral bandwidth with the dominant wavelength varying with the particular chemicals used in their construction. A combination of LED chemistries, each producing photonic energy in a different concentrated spectral band, can be used to tailor production of photonic energy such that a majority of the spectra produced are useful to the target culture and production objectives, rather than wasting energy on non-utilized frequencies.

In addition to their photonic conversion efficiency and spectral specificity, LEDs 207 are physically small, offer flexible mounting configurations, durable long-life cycles, and precise electronic control of intensity and modulation. Conversion efficiency and small physical size allow local light generation, which is less feasible with bulkier, high temperature, wide spectrum alternatives, such as metal halide lamps. Local light generation avoids energy loss incurred while coupling and transmitting remotely generated light to the interface 208. LEDs 207 also have very rapid on/off times and intensity control, which enable very tight restriction of energy use to times in which the photonic energy will be the most useful. This enables close tailoring of light production to the particular stage of growth or production objectives.

This simple photonic energy delivery system is economical to produce and is useful in a wide range of existing applications, such as ponds and raceways for the efficient supply of supplemental light and in bioreactors for which it is the primary source of light.

In the embodiment illustrated in FIGS. 2-7A, the fluid-light unit 206 of this light delivery system 200 is implemented in a photobioreactor, which may be the bioreactor 202. However, the light delivery system 200 can be implemented in any environment adapted to growing target phototrophic organisms. Target organisms include several species of algae and cyanobacteria produced for aquaculture and human and animal food supplements. These species include, but are not limited to *dunaliella, chlorella, nannochloropsis*, and *spirulina platensis*.

The techniques for supplying the non-photonic conditions necessary for growth of these species are known in the art and include: maintaining oxygen at low levels as required by the particular species, maintaining an even temperature to avoid photorespiration, avoiding zenic species, maintaining adequate circulation to ensure even exposure of all organisms in the culture, avoiding heavy metals that can readily be assimilated by some organisms, providing $CO_2$, or sodium bicarbonate at levels sufficient to supplement any gained from the atmosphere, and maintaining pH appropriate for the species. Full descriptions are available in such publications as Barbosa, M. J. G. V., "Microalgal Photobioreactors: Scale-up and Optimization", Doctoral Thesis, Wageningen University, The Netherlands, 2003, p. 161; Richmond, Amos, *Handbook of Microalgeal Culture: Biotechnology and Applied Phycology*, Blackwell Science, Ltd., London, 2004; and Vonshak, Avigad, *Spirulina Platensis (Arthrospira): Physiology, Cell-Biology, and Biotechnology*, CRC Press, 1997.

As shown in the embodiment of FIG. 2, the bioreactor 202 consists of an 18 inch diameter, five foot tall cylinder. In the middle of the bioreactor 202, the air-lift unit 204 and a central column for providing nutrients to the fluid-light units 206 is illustrated. This air-lift unit 204 allows consistent flow without isolated non-circulating zones and is selected to minimize the power necessary to produce an adequate rate of circulation. A pair of synchronized peristaltic pumps, in this case a harvest pump 219 and a nutrient pump 220, introduce a stream of nutrients and ensure harvests of equal volumes of culture. Preferably, the stream of bubbles 212 and the air-lift unit 204 produce a vertical toroidal circulation pattern that draws the culture past the interface plates 208 at the bottom of the bioreactor 202, up the center, and down the sides of the bioreactor 202, i.e., throughout the production space 203. Preferably, the rate of circulation is at least one foot per second to avoid precipitation and should be slow enough to prevent cell damage and avoid wasting power. In one embodiment, the air-lift unit 204 is supplemental to the circulation provided by the rising column of bubbles 212, thus allowing independent control of the nutrient/light feed and the overall rate of circulation.

The fluid-light unit 206, the photonic energy source 205, and the air-lift unit 204 may be manufactured as integral components of the bioreactor 202 or they may be manufactured and installed separately. Preferably, the bioreactor 202 is manufactured with a lid (not shown) to seal the bioreactor during culture production. The lid may be manufactured with or without insulation. When the lid is sealed, light delivery system 200 operates without dependence on the diurnal, seasonal, and geographic limitations of sunlight. Therefore, the light delivery system 200 produces a higher output rate due to 24-hour production by a fixed amount of equipment. Advantageously, algae continuously consume $CO_2$ waste in a 24-hour production facility.

In one embodiment, the air-lift unit 204 is used for circulation of the culture and is fixed to the bottom middle of the bioreactor 202. The air-lift unit 204, using filtered air, is adjustable to achieve the minimum culture medium flow rate necessary to prevent sedimentation of the target organisms or detritus from the organisms. This rate varies with the species and the stage of growth.

The synchronized peristaltic pumps 219, 220 maintain a constant volume of mixed liquid in the bioreactor 202 and are under the control of sensors for bio-mass density and pH. This arrangement operates a continuous operation cycle, but it could easily be operated as a batch or semi-batch system without altering the essential nature of the energy-delivery system described here. The peristaltic pumps 219, 220 are used in order to minimize damage to organisms in the culture.

In one embodiment, the peristaltic pump 220 continuously releases liquid nutrients from a plurality of tubes 224 that open through a manifold just above each interface plate 208. This arrangement is intended to ensure that the nutrients are fully and rapidly mixed into the culture medium. These nutrients can be a high-grade fertilizer, such as F2 or a liquid that is output from intermediate stages of an anaerobic digester. The provision and composition of liquid nutrients is known in the art and any suitable composition may be utilized.

In another embodiment, temperature control is achieved by controlling the temperature of the environment surrounding the bioreactor 202. This is an economical solution when many such bioreactors 202 are enclosed in a single building. Growth up to 8 doublings a day, in certain species of microorganisms, has been demonstrated by the continuous running of the above-described embodiment. Although it is not necessary to provide discrete light and dark periods to produce high growth rates, the present disclosure may be operated to mimic a diurnal cycle. In this implementation, energy costs are reduced by utilizing photonic energy of selected frequencies, by generating the photonic energy locally, and by using LEDs.

In some embodiments, cooling the bioreactor 202 to keep it in the optimal range for culture growth is generally unnecessary. The need is minimized by reducing heating from the absorption of excess spectra and intensities of light, such as commonly occurs with the use of unfiltered solar radiation. Further, the amount of artificial light that is necessary is reduced because the light is uniformly distributed among the culture organisms. Because the culture flows through a chamber of the bioreactor 202, less power is used for producing circulation than in systems that use high flow rates or constricted pipes to combat biofilming or self-shading of a dense culture. Further, a portion of the impetus for circulation is provided by the buoyancy of the bubble stream from the air-lift unit 204 and the fluid-light units 206 that provide the inorganic gas nutrients and the light.

With power costs reduced, the advantages of 24 hour production become economically feasible. These advantages include independence from the diurnal, seasonal, and geographic limitations of sunlight, the higher production rate from a fixed amount of equipment, and a smaller footprint. In addition, the $CO_2$ waste consumption ability of the algae or other autotrophic organisms can stay continuously on line, and, because of the small footprint of the bioreactors relative to ponds, stay local to its source.

The particular form of the bioreactor 202 and the components are adjustable and can be modularized to accomplish efficient manufacture and maintenance. In addition, many bioreactors 202 can be run in parallel to meet industrial and environmental needs Moreover the mass of bubbles 212 resulting from the gas energy-transfer medium provide a distributive surface that is advantageous in dispersing light in low culture densities of early stages of growth. Air is used as the primary component of the energy-transfer medium in the "passive aperture" embodiment because it is simple, economical to produce, and useful in a wide range of existing applications.

Figure 8:
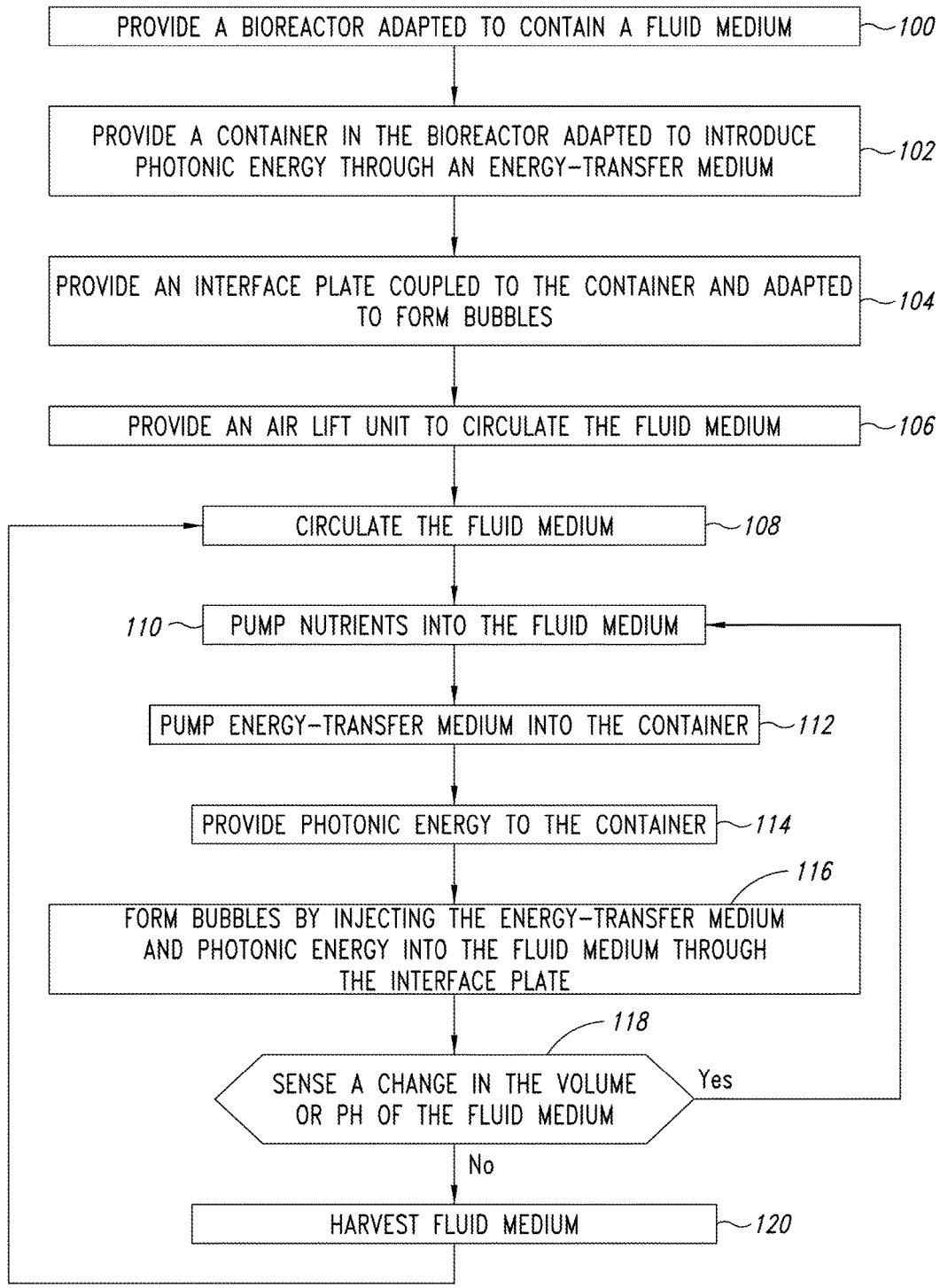
FIG. 8 is a flowchart of an alternate process of delivering photonic energy to a culture.

Referring to FIG. 8, a general overview of an alternative process in accordance with the present disclosure is illustrated. In block 100, the process provides a bioreactor adapted to contain a fluid culture medium. Preferably, the bioreactor is a bioreactor with a diameter of eighteen inches and a height of five feet. However, bioreactors of various sizes and materials may be adapted to adequately house and cultivate the culture medium.

In block 102, the process provides a container in the bioreactor adapted to introduce photonic energy through an energy-transfer medium. The container may be formed of any sturdy and durable material that does not deteriorate in the culture medium. In a preferred embodiment, the container is a weighted circular pot with a diameter of five inches. However, the size and shape of the container depends upon the size of the bioreactor selected and specific characteristics of the energy-transfer medium and of the culture medium.

An interface plate couples to the container in block 104 and contains a plurality of holes through which the energy-transfer medium and photonic energy exit the container in the form of bubbles. The container and the interface plate may be formed with complementary spiral threads so the interface plate securely attaches to the container. However, other suitable methods may be used to couple the interface plate to the container, such as screws, clamps, glue, or the like. The container and interface plate may be manufactured as one component or as individual components for subsequent assembly. Preferably, an air-tight seal forms between the interface plate and the container. The air-tight seal prevents the release of the energy-transfer medium and photonic energy from places other than the holes in the interface plate.

The size and shape of the plurality of holes dictate the size of the bubbles and therefore the amount of the energy-transfer medium and photonic energy injected into the culture medium. The holes may be cylindrical in shape so that the interior rim of the cylinder is the same diameter as the exterior rim. However, the interior and exterior rims may have different diameters in order to more efficiently control the shape of the bubbles produced and to avoid cavitation at a sharp edge. Other materials, such as metal and other plastics, can be used to manufacture the interface plate.

The word "bubble" is intended to cover the injection of photonic energy into the culture medium through a gas or a liquid energy-transfer medium. In the case of an injection of photonic energy through a liquid energy-transfer medium, "bubble" may mean a droplet or drop. Forming bubbles that are too small in the proximity of the culture can produce destructive turbulence.

In one embodiment, the container and interface plate combination securely rests on the bottom of the bioreactor. The container may be weighted or secured by screws, clamps, or any other suitable fastening device. When positioned on the bottom of the bioreactor, the bubbles form and separate from the interface plate traveling vertically through the culture medium. The position of the container may be altered to change the trajectory of the bubbles. For example, the container could be on a motorized base to allow for selective positioning of the container and attached interface plate. Changing the path the bubbles travel can advantageously alter the circulation of the fluid culture medium and thereby more evenly distribute the photonic energy.

In block 106, the process provides an air-lift unit to circulate the fluid culture medium and the energy-transfer medium. Preferably, the air-lift unit is three inches in diameter and circulates the culture at a rate of at least one foot per second to avoid precipitation. Any device that provides circulation, such as rotating paddles or blades, propellers, and peristaltic pumps, may be used in addition to or in place of the air-lift unit.

In one embodiment the bubbles from the air-lift unit and the bubbles from the energy-transfer medium circulate the culture medium. Preferably, the circulation produced is vertically toroidal. A vertical toroidal circulation pattern draws the fluid culture medium over the interface plate and into the rising column of bubbles that provide the surfaces to distribute (reflect, refract, and diffract) the photonic energy evenly among the cells. This arrangement efficiently produces a rate of circulation adequate to avoid precipitation and without isolated non-circulating zones of the fluid culture medium. The rate of circulation should be slow enough to prevent cell damage and limit unnecessary power consumption.

Advantageously, the circulation increases the proportion of the organisms in the culture exposed to the photonic energy. In this circumstance, photonic energy is less likely to be reflected from or absorbed by a limited layer of organisms exposed to the photonic energy source. Additionally, the photonic energy is less likely to be converted into waste heat caused by overexposure of a limited proportion of the organisms. Also, since the origin of the light is not in the culture, the likelihood of occlusion by bio-filming is greatly reduced. The spectra and intensity of photonic energy delivery can be finely controlled, thereby reducing energy costs and avoiding the growth-limiting problems of photo-respiration and excessive heating.

The amount of photonic energy needed to effectively grow the culture is reduced because of the close proximity of light distribution to the organisms. Utilizing only the required spectra and intensity of light minimizes the heating of the culture, and therefore, achieves the optimal temperature range for culture growth more easily. In some circumstances the need for cooling of the culture can be completely avoided.

Blocks 108, 110, 112, and 114 represent the part of the process that mixes, circulates, couples, and/or distributes the energy-transfer medium and the photonic energy to the culture. More particularly, the photonic energy is transmitted into the fluid culture medium through the controlled gas or liquid energy-transfer medium as the controlled gas or liquid is releasing from the interface plate. In block 108, the process circulates the fluid culture medium contained in the bioreactor. The circulation may be provided by any combination of the bubbles from the air-lift unit, the bubbles of the energy-transfer medium, and any other suitable circulation device.

In block 110, the process pumps nutrients into the fluid culture medium. Pumps either internal or external to the bioreactor provide the nutrients. In a preferred embodiment, the nutrient pumps are peristaltic.

In block 112, the process may pump filtered air and the energy-transfer medium into the fluid-light unit. The energy-transfer medium may contain $CO_2$, $N_2$, or other gaseous nutrients. The bioreactor may be manufactured with the pumps as an internal component or the pumps may be an external feature attached to the container through flexible piping.

In block 114, the process provides photonic energy to the fluid-light unit. Photonic energy is energy in some part of the visible spectrum (380 nm-700 nm) of light that is useful to autotrophic organisms.

The source of the photonic energy provided to the fluid-light unit may be entirely artificial, solar, or a combination of both. Because the energy-transfer medium forms a barrier, no part of the fluid culture medium is in contact with or exposed to the source of photonic energy. An array of LED lamps 207 may be the photonic energy source that delivers light to the fluid-light unit. Using LED lamps 207 of selected frequencies in the critical red and blue regions of the spectrum reduce energy costs because no energy is wasted on frequencies that are not used by the phototrophic organisms. Artificial sources include a solid-state source, a gas-discharge source, and an incandescent source, or any other controllable photonic energy source. The photonic energy may be produced or captured remotely and delivered to the container by fiber optics, light pipes, waveguides, or other light-transmission means.

Optionally, the energy-transfer medium is introduced into the culture medium without having been previously illuminated. The bubbles thus formed then can scatter light introduced through a different aperture that is protected by flowing energy-transfer medium or introduced from some other photonic energy source. It is to be understood the nutrient-energy distribution process may be operated 24 hours a day without dependence on the diurnal, seasonal, and geographic limitations of sunlight. Advantageously, in a 24-hour production facility, phototrophic organisms can continuously consume $CO_2$ waste.

Block 116 describes the process of forming bubbles in the fluid culture medium. As the process provides the energy-transfer medium, i.e., a nutrient-gas/filtered-air mixture, and the photonic energy to the fluid-light unit, pressure accumulating in the fluid-light unit causes the energy-transfer medium to pass through the holes in the interface plate. Bubbles of the energy-transfer medium will rise in the fluid culture medium due to the disparate densities of the materials. Movement of the bubbles generates movement of the fluid culture medium and enhances distribution of the photonic energy throughout the fluid culture medium.

Block 118 describes the process of sensing a change in the volume or pH of the fluid culture medium. Sensors may provide feedback to the pumps and other devices in and around the bioreactor to regulate parameters of the growth environment. Block 120 provides for a harvesting of the fluid medium when organisms in the culture medium are in a desired state.

This method addresses the problems of turbidity by distributing light throughout the culture as the culture is circulating. Bio-filming is avoided by providing light to the culture without having the photonic energy source in direct contact with the culture. Advantageously, this method reduces power consumption and makes 24-hour production of photosynthetic organisms economically feasible.

Optimized Energy-Transfer Medium Embodiment

In the "optimized energy-transfer medium" embodiment, the efficiency of light transfer is improved by controlling coupling characteristics of the energy-transfer medium itself. A large mismatch between the refractive indices of the photonic energy source, the energy-transfer medium, and the culture medium results in lossy effects, which include reflectance back at the photonic energy source, reflectance back into the aperture, and light scatter within the energy-transfer medium. These losses can be reduced by selecting the energy-transfer medium to have a refractive index closely matched to the photonic energy source and the culture medium, or an intermediate index which smoothes the gradient between the photonic energy source and culture medium indices.

Alternatively, under certain circumstances, an intentional refractive index mismatch could be employed to increase dispersion of light as it crosses the boundary between the two media, resulting in more organisms exposed to the projected light and thus increased efficiency of energy use. This deliberate mismatch would be used in a case where the culture density is low and therefore subject to transmission of photonic energy through the culture medium without hitting receptive organisms.

In addition to refractive index control, properties of the inherent lens, bubble 212*a*, formed at the boundary of the energy-transfer and the culture media can be modified by controlling immiscibility between the media (see FIGS. 7 and 7A). Immiscibility is largely dependant on differences between the energy-transfer and the culture media in properties such as specific gravity, viscosity, and surface tension. Some controls to adjust immiscibility include incorporation into the energy-transfer medium of a surfactant to change surface tension or an emulsifier to modify viscosity.

Coupling inefficiencies can consume up to 40% of photonic energy injected into the culture medium. For the culture media used in most commercial applications, a reasonable approximation to matching the refractive indices can be achieved by using filtered water as the energy-transfer medium Therefore, use of filtered water as the energy-transfer medium is advantageous in decreasing the coupling inefficiencies. The rate of flow of the water into the culture medium can vary over a wide range as long as flow is sufficient to maintain a barrier between the culture medium and the photonic energy source.

In one embodiment, the fixed lens of the LEDs 207 in the photonic energy source 205 is embedded in the stream of the filtered water before the water enters the culture medium. The filtered water acts as a temporary replenishing lens for light transmission. However, in many commercial applications in ponds or raceways, the cost and limited availability of filtered water would offset at least part of the savings from the more efficient coupling, making a gaseous energy-transfer medium a more economical choice.

Control of energy-transfer medium properties can also be used to enhance instrumentation measurement accuracy and effectiveness. For example, light can be measured with a higher signal-to-noise ratio by matching refractive indices, which will minimize reflections generated by transmission across medium boundaries and reduce scatter within the energy-transfer medium itself. Also, the stability of the lens surface formed by the boundary between the energy-transfer and the culture media can be enhanced by controlling the immiscibility of the energy-transfer medium relative to the culture medium. Such stability means that the lens is less vulnerable to surface distortion created by turbulence from the circulating culture medium. Both interventions will reduce system noise from stray light and result in improved accuracy and stability of measurements.

For measurement applications, the energy-transfer medium may be composed of 1.5% xantham gum and filtered water. This combination provides a very stable lens/window through which light can be projected or received. In this embodiment, the dispersal of a large amount of light into the culture is not the objective rather; the objective is to acquire data through measurements. Therefore, the energy-transfer medium is injected into the culture medium at a sufficiently slow rate to just maintain a stable window and a protective barrier between the instrumentation and the culture medium. In one example, an aperture size necessary to expose a standard photodiode requires an injection rate of 1 cm per minute.

Flow Control of Energy-Transfer Medium Embodiment

In the "flow control" embodiment, adjustment for varying conditions in the properties of the energy-transfer medium, the culture, and the environment of the culture require maintaining a controlled flow of energy-transfer medium. Controlling the flow of energy-transfer medium is important for controlling photonic energy delivery into the culture medium. As described above in the "optimized energy-transfer medium" embodiment, optimizing different conditions requires changing properties of the energy-transfer medium, such as viscosity or surface tension. Adjusting the viscosity or surface tension can vary the flow of the energy-transfer medium into the culture medium. In addition, variations in properties of the culture medium due to density of cells or types of organisms can change the ease of flow of the entering energy-transfer medium.

Environmental changes, such as ambient temperature or the depth of the fluid-light unit's in the culture medium can affect the flow of the energy-transfer medium. The flow for a particular fluid-light unit can also be affected by its position in the supply line when several units are serviced by a single supply line. In addition, the flow of the energy-transfer medium can be deliberately altered by the operator in response to cost of the materials in the energy-transfer medium or the needs of the culture. Each of these factors produces variation in the flow of energy-transfer medium that must be controlled to maintain good control of the delivery of photonic energy.

Figure 9:
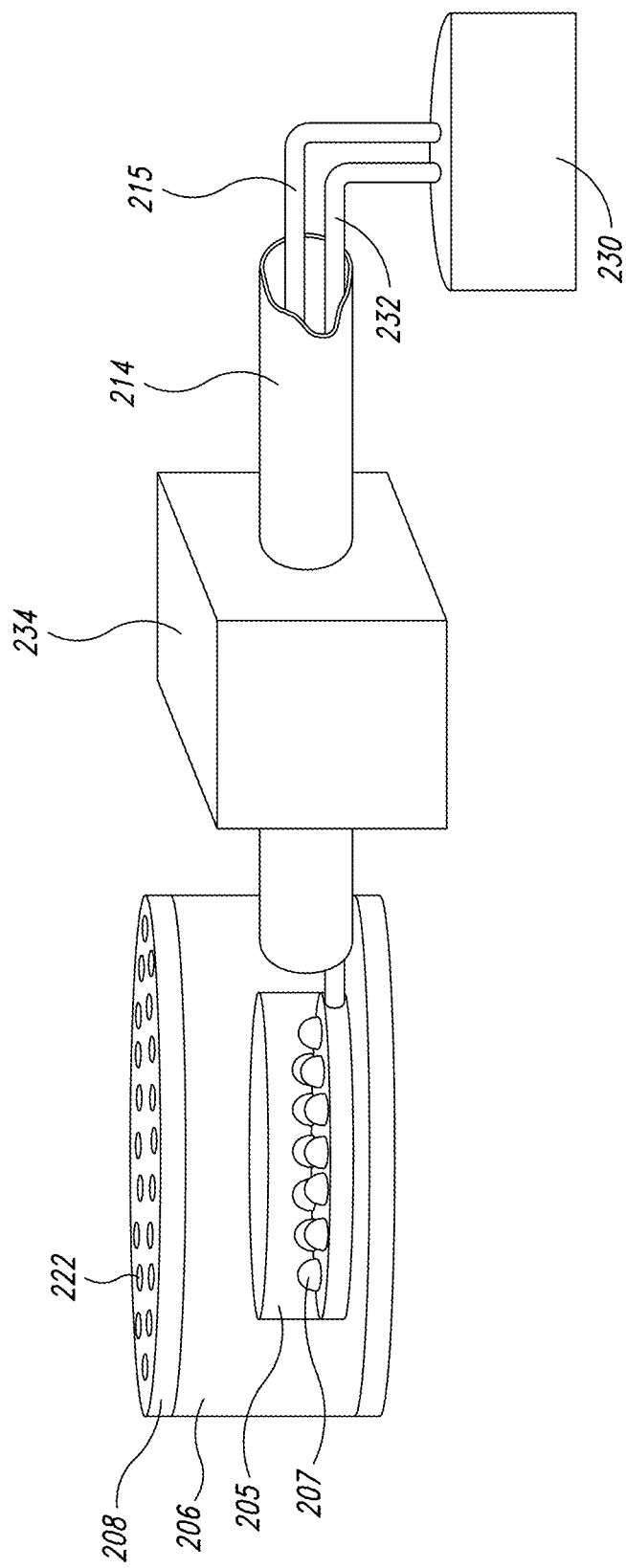
FIG. 9 is an enlarged isometric view of another embodiment showing a localized light source and energy-transfer medium flow control in the fluid-light unit of FIG. 4.
Figure 10:
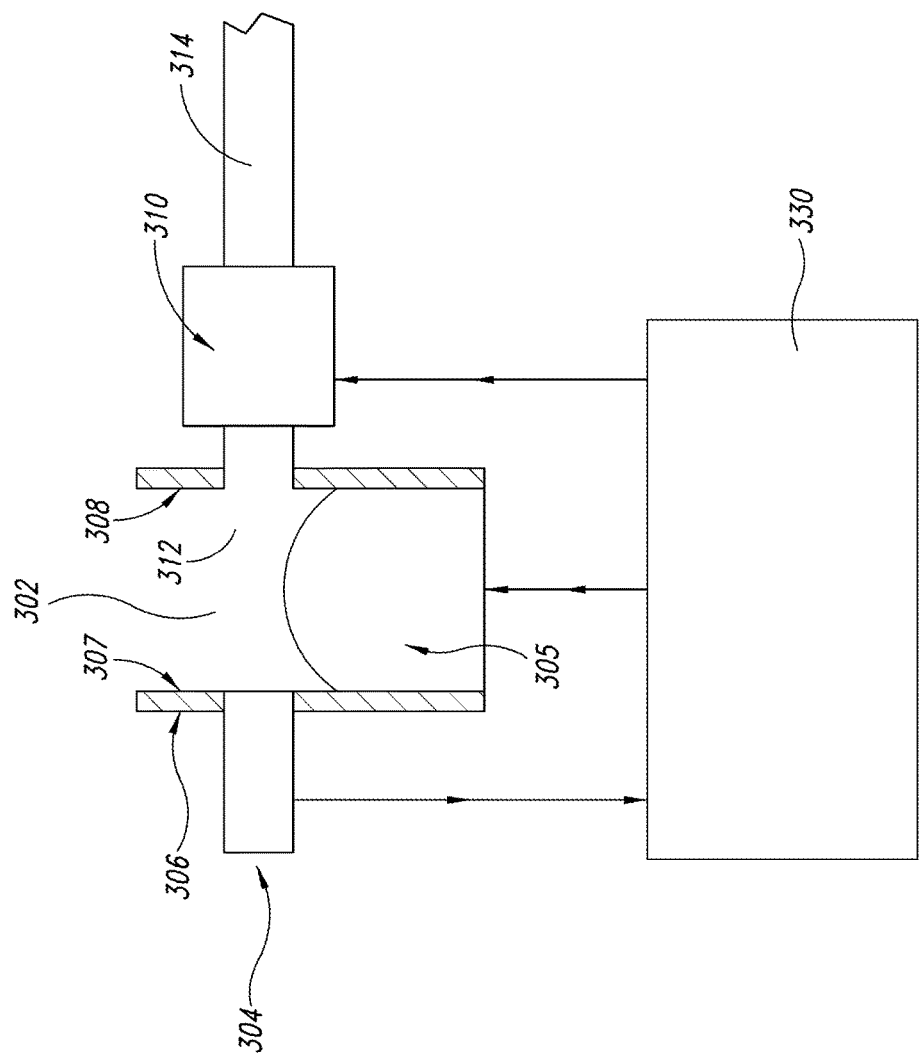
FIG. 10 is a diagram of a controlled aperture according to another embodiment of the present disclosure.

The flow of the energy-transfer medium may be controlled before entry into the fluid-light unit 206, as shown in FIG. 9, or the flow of the energy-transfer medium may be controlled at each individual hole or aperture, as shown in FIG. 10.

FIG. 9 illustrates an embodiment of the fluid-light unit 206 where the flow of the energy-transfer medium is controlled by an electronic flow controller 234. The electronic flow controller 234 may be attached to the piping 214 connected to the fluid-light unit 206 to control the rate of introduction of the energy-transfer medium. The second conduit 232 may provide the electronic flow control drive from the process controller 230 through the piping 214.

Alternatively, the electronic flow controller 234 may be attached externally to the production space 203 of the bioreactor 202.

The flow of energy transfer medium into the fluid-light unit 206 and into the culture medium may be adjusted to optimize the coupling of photonic energy into the culture. The electronic flow controller 234 modulates the pressure and duration of the flow of the energy-transfer medium. Additionally, the electronic flow controller 234 may be synchronized with other electronic flow controllers along a supply line to optimize the delivery of the energy-transfer medium to each bioreactor (see FIG. 16).

As illustrated in FIG. 10, one method of controlling flow into the culture medium includes using piezo or MEMS valve technology to make each aperture 302 in the interface active and controllable. The fluid-light units 206 described with respect to FIGS. 2-9 may be modified to include controllable apertures, such as those illustrated in FIG. 10. This increases efficiency by synchronizing light source modulation with the momentary state of the energy-transfer medium. In addition, the controllable aperture 302 provides a means to control the pressure and duration of energy-transfer medium flow and the spectra, intensity, and duration of the light provided. Sensors 304 may provide feedback indicating when a bubble forms and releases from the interface plate 208.

The single aperture 302, which may be used in an array of apertures of various shapes and sizes in the fluid-light unit 206, may be separately controlled by the sensor 304 to release energy-transfer medium to optimize coupling of the light with the formation of the bubble. The controllable aperture 302 allows an operator to have fine localized control down to an individual aperture or a small group of apertures. In the case of individual aperture control, it would be possible to carefully control the energy-transfer flow rate from one bubble or drop per every few seconds to many bubbles or drops per second.

The aperture 302 may be a hole formed through an interface 306, which may be similar to the interface 208 illustrated in FIGS. 4-6. The sensor 304 may be positioned on an internal surface 307 of the aperture 302 so that the sensor 304 is not obstructed by the interface 306. On an opposing internal surface 308 an opening 312 through interface 306 allows the energy-transfer medium to enter the aperture 302. The energy-transfer medium may flow through a flexible pipe 314 where the flow is controlled by a flow regulator 310, which may be a piezo or MEMs valve. LEDs 305 can be turned on and off sufficiently rapidly to make it valuable to know the state of bubble or drop formation so that the photonic energy source is only activated when the bubble or drop is at a state that effectively couples light into the culture medium. Consequently, the amount of time that light is delivered can advantageously be finely tuned to particular applications and stages of growth. Such control can minimize energy wasted from reflectance, which varies with the density of the culture, back into the photonic energy source.

In this particular embodiment, the single, electronically controlled, flow regulator 310 is installed in each fluid-light unit 206 which maintains a constant flow of energy-transfer medium through the group of apertures 302 from the fluid-light unit 206 into the culture medium. The flow regulator 310 may be a MEMS or piezo technology to offer very rapid and precise control of the flow.

Electronic control of the flow regulator 310 is achieved with a typical computer, such as process controller 330, used for simple industrial process control. The process controller 330 may control and process information from the sensor 304, to the light source of LEDs 305, and to the flow regulator 310. The sensor 304 may provide feedback about dynamic pressure, light reflectance change in order to determine an optimal flow rate, and timing of the LEDs 305 to synchronize the flow and provision of light. The sensor 304 may assist in providing a high efficiency coupling of the energy-transfer medium into the culture medium. In addition, this process controller 330 allows an operator to set flow parameters based on a desired rate of energy-transfer medium consumption, changes in composition of the supplied energy-transfer medium, cost or availability of the energy-transfer medium, growth stage of the organisms being cultured, process metrics, and production objectives.

Once programmed, the flow regulator 310 makes automatic adjustments, which adapt to varying influences on flow rate. Such influences include position on a multi-drop supply line, changes in ambient temperature, depth of the fluid-light unit 206 in the culture medium, and varying density of the culture in the culture medium. Electronically controlled flow regulators 310 are readily available standard pieces of industrial process control equipment and will not be described in detail. Use of these programmable flow regulators 310 to meter delivery of the energy-transfer medium allows effective optimization of light delivery to cultures in the culture medium.

Combinations of the described embodiments provide additional benefits. For example, the controlled flow embodiment and the optimized energy-transfer medium embodiment can be used together to produce replenishing lens surfaces of various sizes and refresh rates, varying decay times following release from the aperture, and increase extension lengths into the culture medium while attached to the aperture. Control of the inherent lens formed at the boundary of the injected energy-transfer medium and the culture medium provides the capability to project photonic energy with high efficiency into the culture medium at beam angles ranging from narrowly focused for greater reach into the culture medium, to broadly disperse for near field illumination. Further, by careful selection of injection parameters and energy-transfer medium properties, this control can be achieved over a wide range of aperture sizes, which provides flexibility in the positions of the photonic energy sources 205 that will lead to efficient energy coupling.

Spectral Control Embodiment

In the "spectral control" embodiment, conservation of photonic energy, reduction of heat loading, as well as optimizing production of biomass or various metabolites is accomplished by close control of the spectral content of light distributed to a culture.

Reference throughout this specification to "spectral content" for defining frequency dependant qualities of the light source is an inclusive term for more specific measures including spectra, spectrum, spectral intensity, spectral density, power spectral density, and spectral distribution. "Spectral content" may also be used to refer to frequency dependant qualities of light in place of some more specific terms such as "spectral distribution" and "spectral density" to avoid confusion with the concepts of light distribution and culture density.

A general region of photosynthetically active radiation (PAR) is defined to be within the visible spectrum of light in the range of 400 to 700 nm. Phototrophic organisms can only effectively utilize a limited range of light frequencies within the PAR region. Providing spectral content with an emphasis on blue light is advantageous because it is the peak absorption range for the major photo-pigments, i.e., chlorophyll a, chlorophyll b, and carotenoids. Healthy growth requires delivery of some spectral content outside the blue region to support important carotenoids and accessory pigments, such as chlorophylls c, d, and e, which have slightly longer wavelength absorption peaks. Additionally, the pigments chlorophylls a and b that have primary absorption peaks in the blue region also have secondary absorption peaks in the red region of the spectrum. Providing these pigments with an increased proportion of red light can be beneficial when organisms are developing lipids.

Tailoring spectral content is also useful when targeting a probiotic combination of organisms such as the case of growing cyanobacteria with algae. Cyanobacteria require some additional spectral content in the middle of the PAR region to fulfill photonic energy requirements of phycolibins (e.g. phycocyanin and phycoerythrin).

Delivery of photonic energy with spectral content not productively absorbed and utilized by the target organisms has the deleterious effects of heat loading the growth environment and causing target organisms to divert energy from productive growth to protective mechanisms for shielding against potentially destructive photonic radiation. It is therefore advantageous to only deliver photonic energy with spectral content useful to the organisms at their current stage of growth. It is also optimal to limit production of photonic energy from an artificial source to only include spectral content useful to the target organism and avoid wasting energy to generate photonic energy with no productive value.

There are several ways to control spectral content of light delivered to the target organisms. One is to select an artificial light source designed to produce the desired spectral content. A second approach is to combine a group of individual artificial light sources with varied spectral content to form an array that collectively produces the desired spectral content. Further refinement and dynamic adjustment of spectral content can be gained through electronic control of individual light sources within the array. Another approach is to filter a broad spectrum light source to limit delivered spectral content to a useful set of target frequencies. Yet another approach is to employ technologies such as quantum dots, metal halide salts, and phosphors to convert or shift non-productive wavelengths to spectral content productive to organism growth.

Deployment of spectral content control technologies for growing cultures in an efficient production environment have been limited by constraints imposed from biofilming and turbidity of the dense culture. Biofilming of the light source not only wastes energy, precluding use of artificial light in cost sensitive applications, but also changes the spectral content delivered to cultures in the culture medium as a result of selective absorption from adhering organisms forming the biofilm. Inefficiencies in light delivery can easily require ten times the photonic energy to achieve a similar organism growth rate produced in a system without these losses. The increased demand on photonic energy delivery limits use of most spectral content control technologies to applications that are not particularly cost sensitive. In some cases mitigating the effects of biofilming and turbidity has dictated a growth environment topology that introduces a different and often larger set of production inefficiencies. An example is a shallow, large surface area pond or raceway. The pond or raceway will require a large area filter to provide spectral content control that is likely to be cost prohibitive for a majority of applications.

The disclosed method delivers light to the set of organisms in the culture medium through the flowing energy-transfer medium that separates the light source from the culture medium. As the energy-transfer medium flows into the culture medium it breaks into many bubbles or drops to form a distribution array that scatters delivered light widely within the culture medium. The disclosed method of light delivery prevents biofilming of the light source and provides even distribution of light in the turbid dense culture. Solving these problems dramatically increases light delivery efficiency and opens cost sensitive applications to the use of artificial light and deployment of spectral content control technologies.

Artificial light sources offer a wide range of spectral content control. A group of individual artificial light sources with varied spectral content can be combined to form the light source array that collectively produces the desired spectral content. Electronic control can be used to change the contribution of individual light sources within the array and provide dynamic adjustment of spectral content in response to changing phototrophic needs of the target organism. Spectral content can also be adjusted in response to energy cost at different times in the day. Artificial production of photonic energy in the blue region is very efficient. During the hours of peak energy cost, predominantly or exclusively blue light can be produced and delivered to the target culture. Less efficient red and other fill spectra can be provided or increased during hours of lower energy cost. LED technology provides an efficient artificial light source with limited spectral content per given chemistry. LEDs with different chemistries can be combined to create the array of artificial light sources with varied spectral content.

Referring to FIG. 6, one "spectral control" embodiment shows the array of LEDs 207 deployed as the photonic energy source 205 and filtered air is utilized as the energy-transfer medium in the fluid-light unit 206. The LED array 207 has two independently controlled drive channels that are separated from the energy-transfer medium by the conduits 215 and 232. The conduit 215 attaches the blue LEDs 228 to the process controller 230 and provides the independently controlled drive channel. Ideally, the blue LEDs 228 have a spectral output centered at 465 nm. The second conduit 232 attaches the red LEDs 226, ideally centered at 660 nm, to the process controller 230 providing the other independently controlled drive channel.

The LEDs 226, 228 are selected such that when both channels are fully driven, there is a total radiant energy of 10 watts with a radiant energy ratio of 2:1, blue to red. Independent control of intensity and on/off duration for each color channel is implemented with an industrial computer, process controller 230, typical of simple industrial process control applications. Total radiant energy and the ratio of blue to red are adjusted to reduce energy usage during periods of peak energy cost. In addition, continual process metrics are used as a basis for adjustment of the spectral distribution to maintain healthy metabolic activity of the culture or to target specific production objectives, such as an increase in red light to promote lipid production.

Some artificial light sources such as metal halide gas discharge lamps, provide very efficient sources of photonic energy but do not have the narrow spectra of LEDs. A large portion of the spectral content are in areas that are either not useful or are harmful to the target organisms. Light from such a source can be filtered by controllable dichroic filters by reflecting the unproductive heat and spectra to another process, such as photovoltaic cells or heat engines.

Another approach to control of spectral content of the light source is to filter or isolate a set of frequencies from a broad spectrum source. Filtering or isolation is used to limit the spectral content of delivered light to only contain wavelengths which can be absorbed and utilized by the target organisms. A particularly useful broad spectrum photonic energy source is solar radiation from the sun. When solar radiation is available, a combination of dichroic mirrors or other light splitting technology can be used to isolate a first set of frequencies to produce the light source only containing wavelengths useful for growth of the target organism. The light source formed by the first set can then be coupled into a waveguide and distributed to the organisms in a remote growth environment. The remaining frequencies isolated from the first set, form a second set containing energy unproductive to growth of the target organisms. Energy contained in the second set can be directed to other processes such as conversion to electrical energy by photovoltaic cells or production of mechanical energy from a heat engine.

This approach to delivering filtered solar energy tailored for the target set of organisms and utilizing the remaining solar energy for a secondary process, optimizes culture growth from solar energy and offsets a portion of operating costs through generation of useful energy. A further increase in culture growth rate can be achieved through 24-hour production. Implementation of a hybrid photonic energy source may consist of filtered solar light and an artificial light source that provides a 24-hour light source optimized for efficient production of phototrophic organisms. The filtered solar light may be captured remotely and delivered to the growth environment through a wave guide while sunlight is available. To improve efficiency, the artificial light source may have a spectral content control and may be produced locally to the growth environment.

Many of the advantages gained by spectral control of the light delivered to a set phototrophic organisms are well known in the industry. These include conservation of photonic energy, reduction of heat loading in the growth environment, as well as optimizing production of biomass or various metabolites. The disclosed method of light delivery improves efficiency to the point where artificial production of light and deployment of technologies for control of spectral content becomes available to wide range applications.

Instrumentation Aperture Embodiment

Figure 11:
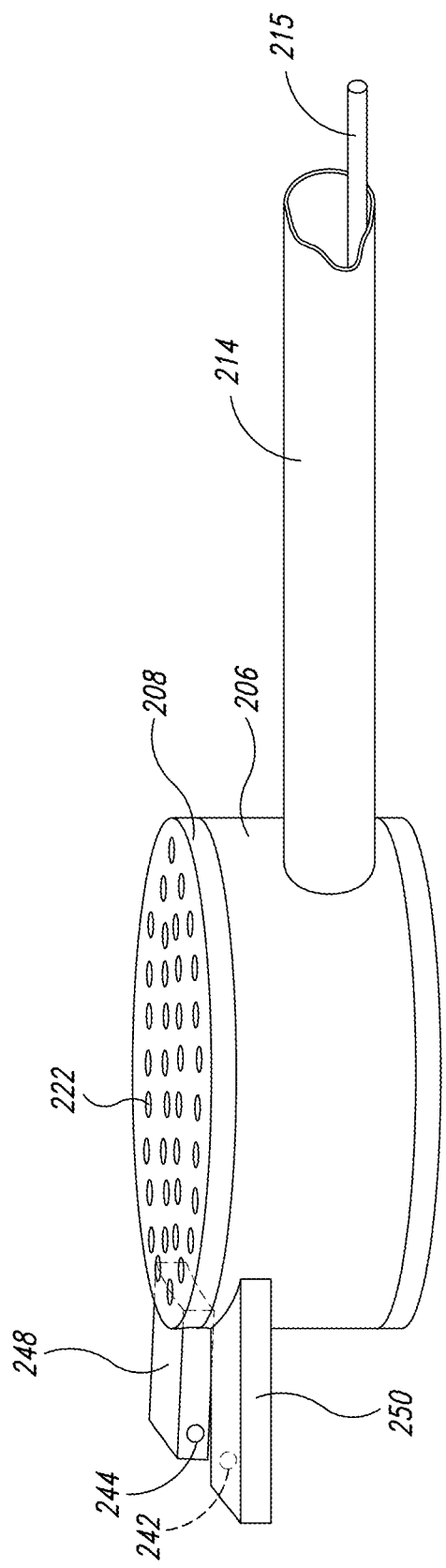
FIG. 11 is an enlarged isometric view of another embodiment of the fluid-light unit of FIG. 4 having measurement instrumentation attached.
Figure 12:
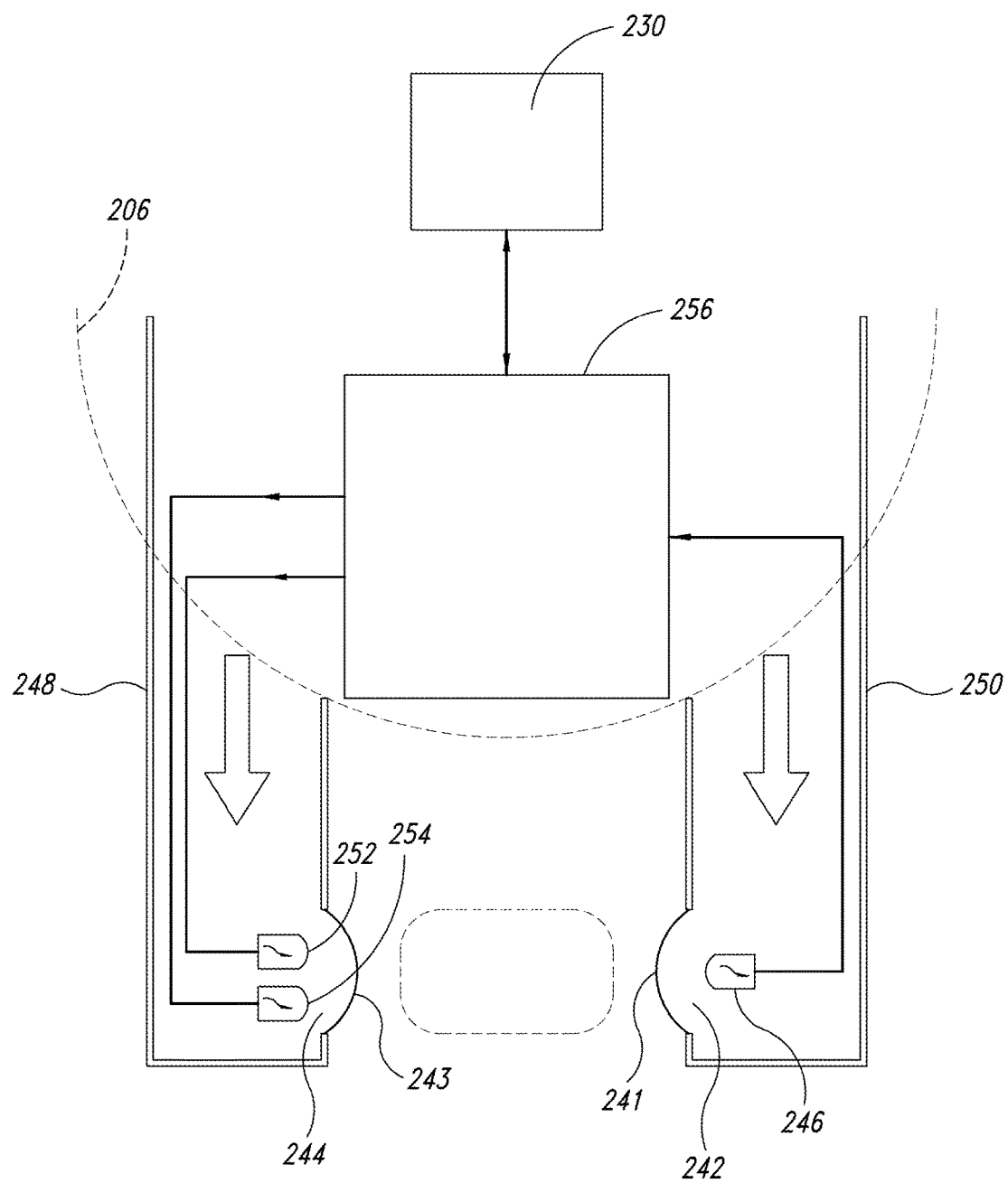
FIG. 12 is a cross-sectional top view of the measurement instrumentation of FIG. 11.

In the "instrumentation aperture" embodiment, transmission of photonic energy through the fluid energy-transfer medium can also be used for measuring important parameters related to culture growth. As illustrated in FIGS. 11 and 12, light can be projected from one aperture 244 in an instrumentation arm 248, through the culture medium, toward a photoreceptor 246 stationed in another aperture 242 in an adjacent instrumentation arm 250. The instrumentation arms 248, 250 may attach to the exterior of the fluid-light unit 206 so that as the culture medium passes by the fluid-light unit 206 the photoreceptor 246 can measure selective parameters of the culture medium.

The photoreceptor 246 can measure the selective absorption of certain frequencies. For example, green frequencies are relatively poorly utilized by microorganisms currently in commercial production. The photoreceptor 246 can detect decreases in the amount of green light received, which thereby provides a measure of the increasing density of organisms in the culture.

In contrast, light in the blue region is more likely to be absorbed by chlorophyll a, chlorophyll b, or carotene pigments. The contrast in the differential absorption of blue and green light provides a coarse but inexpensive measure of photosynthetic activity. More elaborate control of the frequencies projected and careful measurement of the frequencies received can be controlled to selectively measure the activity of a variety of photo-sensitive pigments. The selective absorption of the frequencies or the frequency shifts resulting from florescence are measurable parameters. These measures of culture density and photosynthetic activity allow more efficient allocation of spectra and intensity of light depending on the stage of growth and organisms being cultivated.

However, both the photonic energy source and the photoreceptor 246 in such measurements are subject to biofilming if they are directly exposed to the culture medium. One current method, which can be used to avoid deleterious effects from biofilming of measuring instrumentation, involves periodically collecting discrete samples of the culture-containing culture medium followed by cleaning of the instrumentation between samples. This effectively avoids biofilming by allowing only brief exposure of the instrumentation, but it is labor intensive and does not lend itself well to high frequency sampling or automation.

Advantageously, the flowing energy-transfer medium separating the culture medium from the photonic energy source at the projection location (i.e., the interface plate 208) and from the photoreceptor 246 at the receiving location solves the problem of biofilming and allows continual, automated, and on-line monitoring for responsive process control. More particularly, the energy transfer medium may pass through the arms 248, 250 and form replenishing lenses 241, 243 at the apertures 242, 244, respectively. In the illustrated embodiment of FIGS. 11 and 12, the projection aperture 244 and the reception aperture 242 may be placed approximately 5 cm apart. This distance is a compromise that allows enough culture to pass between the two apertures 242, 244 to allow measurement at an early stage of growth and still allows sufficient light to pass through a dense culture to allow measurement in a later stage of growth. The exact distance could be modified to adapt to different circulation conditions.

In one embodiment, a blue projection light 252 is provided by an LED centered at 465 nm and a green projection light 254 is provided by an LED centered at 530 nm. The photoreceptor 246 can be a standard photodiode or any other suitable photoreceptor. The energy-transfer medium may pass through the arms 248, 250 to exit at both apertures 244, 242 to create an interface between the projection lights 252, 254, the photoreceptor 246, and the culture medium. In one embodiment, filtered water may flow through the arms to prevent biofilming at the apertures 242, 244. The projecting and receiving apertures 242, 244 are mounted on arms 248, 250 that may extend from the side of the fluid-light unit 206 parallel to the interface plate 208. This placement allows measurement without the noise and turbulence provided by the bubbles or drops of energy-transfer medium rising into the culture medium.

Various colors may be selected for the light sources 252, 254 to meet the needs of a particular environment. Other types of instrumentation may replace the photoreceptor 246, such as a camera or an infrared instrumentation device. For example, the instrumentation may be configured to continually sample density or look for changes in photosynthetic parameters.

In an alternative embodiment, a single arm may be provided that incorporates instrumentation directed to collecting measurements by reflection from the culture medium. The single arm may have more than one aperture so that multiple components on the single arm interact with the culture. Together, these embodiments of the flowing energy-transfer medium provide a wide range of control mechanisms to optimize the delivery of light. The specific measures taken to optimize photonic energy coupling will depend on system variables such as, specific needs of the organisms being cultivated, properties of the culture medium, density of the culture in the culture medium, incorporation of nutrients into the energy-transfer medium, shape and size of the environment adapted for growing cultures, rate and method of culture medium circulation, and production objectives.

Distribution Array Embodiment

Figure 13:
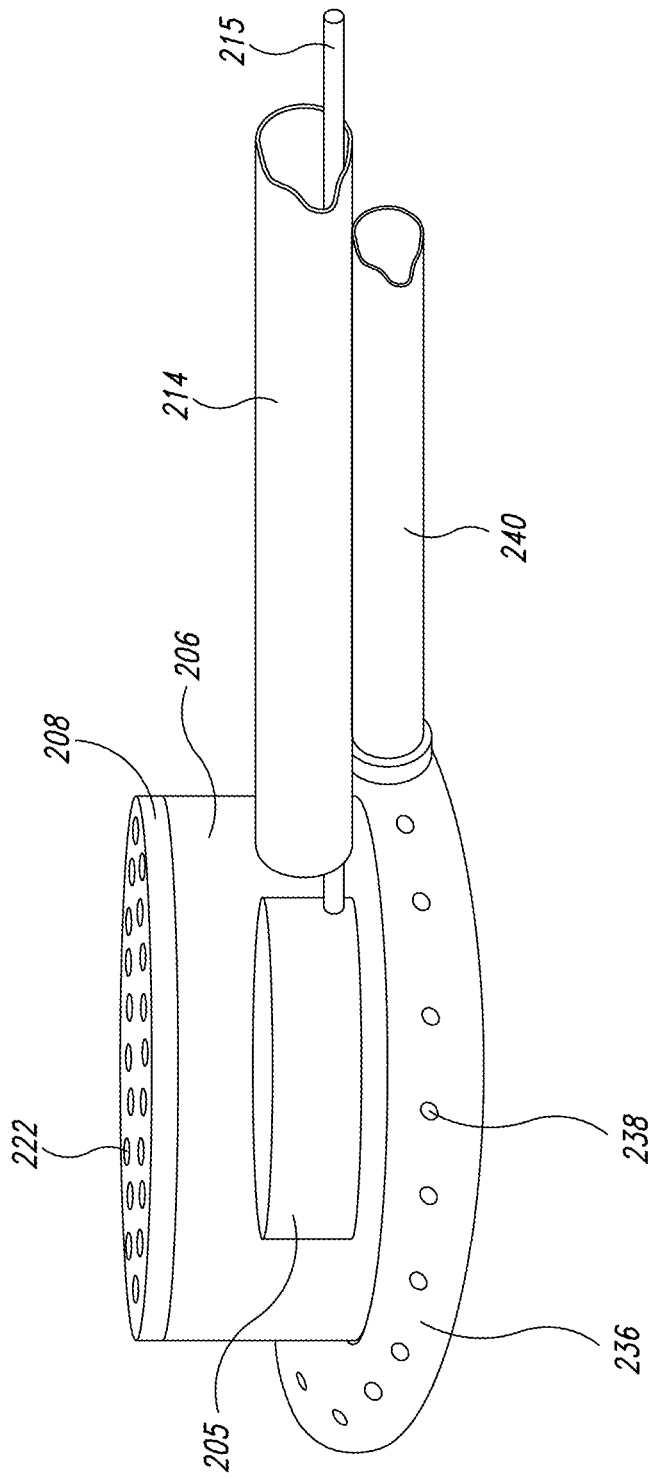
FIG. 13 is an enlarged isometric view of another embodiment showing a remote distribution array generator on the fluid-light unit of FIG. 4.

As described above, the energy-transfer medium serves several functions, which include, but are not limited to: providing a conduit for the transmission of photonic energy into the culture medium, shielding the photonic energy source 205 from the effects of biofilming, distributing light into the culture by acting as a source of lenses, such as bubble 212a that replenish themselves and therefore are not subject to biofilming, and distributing light through the culture by breaking into many bubbles 212 or drops that scatter incident photonic energy where "scatter" means at least one among reflecting, refracting, and diffracting the incident light (see FIGS. 7, 7A, and 13). This scattering decreases vulnerability to self-shading in a very dense culture. In this function, the energy-transfer medium provides a "distribution array" into which the photonic energy is projected for the purpose of scattering light.

In the "distribution array" embodiment, one energy-transfer medium is optimized for providing a photonic energy distribution array and a different energy-transfer medium is optimized for providing a transmission conduit from the photonic energy source 205 into the culture medium. As described above, it is advantageous in some circumstances, to provide the energy-transfer medium with optimized light coupling properties. It is additionally advantageous to provide the "distribution array" that scatters the photonic energy once it enters the culture medium. A gaseous energy-transfer medium injected into the culture medium, producing rising bubbles, can function as the effective distribution array. However, the gaseous energy-transfer medium does not necessarily provide the most efficient light transmission conduit from the photonic energy source into the culture medium. An additional energy-transfer medium may be used to provide the array of bubbles that scatter and evenly distribute the incident light within the culture medium. These energy-transfer media jointly introduce and distribute photonic energy into the culture, but can be separately optimized.

FIG. 13 illustrates an embodiment of the "distribution array." The fluid-light unit 206 as described above may provide the energy-transfer medium that provides the array of bubbles that scatter and distributed light in the culture medium. The fluid-light unit 206 may have the interface plate 208 with holes 222 attached, which may shield the photonic energy source 205 from the culture medium. As described above, piping 214 attaches to the fluid-light unit 206 to feed the energy-transfer medium into the fluid-light unit 206. The conduit 215 may pass through piping 214 to couple the photonic energy source 205 to the process controller 230 (see FIG. 6).

The embodiment in FIG. 13 is intended for a relatively deep container, such as the bioreactor 202 described above. Filtered air enters the culture through a ring-shaped pipe 236 that has a line of closely-spaced holes 238, $\frac{1}{16}$ inch in diameter. This ring-shaped pipe 236 fits around the fluid-light unit 206 having the interface through which the energy-transfer medium coupling the photonic energy flows. The ring-shaped pipe 236 may be placed approximately two inches below the interface plate 208 and depends on the rate of flow of the energy-transfer medium. This allows the array of bubbles to form and rise into the path of the energy-transfer medium that is introducing the photonic energy and thus optimizes the "distribution array's" ability to scatter and distribute light through the passing culture.

Figure 14:
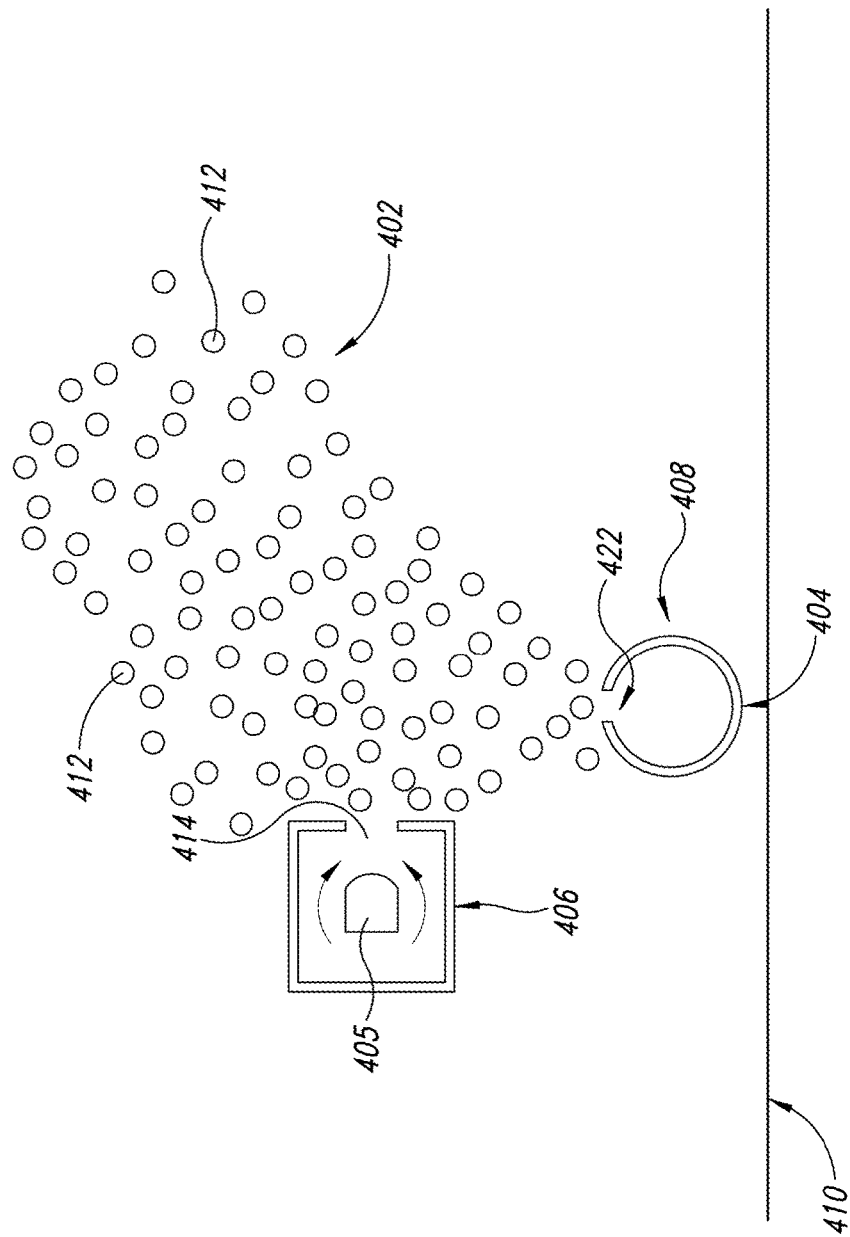
FIG. 14 is a cross-sectional view of a system for providing light to a culture a shallow growth environment, according to another embodiment of the present disclosure.

A supply pipe 240 couples to the ring-shaped pipe 236 and provides the energy-transfer medium that distributes the photonic energy. The supply pipe 240 may provide filtered air to the ring-shaped pipe 236 so that bubbles will form at the holes 238 spaced around the ring-shaped pipe 236. The filtered air may include nutrients. FIG. 14 shows an alternative embodiment intended for placement in a raceway that is relatively shallow. Filtered air is used as the energy-transfer medium to function as a distribution array 402 introduced into the culture medium through an aperture pipe 404 that has a line of closely-spaced holes 422 $\frac{1}{16}$ inch in diameter. This aperture pipe 404 is placed orthogonal to the flow of the energy-transfer medium that is introducing the photonic energy from a photonic energy source 405 in a light distribution unit 406. A gas or liquid energy-transfer medium may be fed into the light distribution unit 406 to couple the photonic energy into the culture. The light distribution unit 406 includes an aperture 414 where the energy-transfer medium couples the photonic energy. Utilizing liquid energy-transfer medium will cause less reflection back to the photonic energy source 405, less internal scatter before entering the culture medium, and the possibility of allowing a larger aperture and acceptance angle.

The placement of the aperture pipe 404 is as close as possible to a bottom 410 of the shallow environment without being clogged by sediment, and approximately two inches downstream from the photonic-energy aperture 414. The downstream distance from the photonic-energy aperture 414 can be adjusted dependant on flow rate of the culture medium in the raceway. This allows the array 402 of fine bubbles 412 to form and rise into the path of the photonic energy being introduced, thus optimizing the "distribution array's" ability to scatter and distribute light through the passing culture. The dynamics of bubble 412 formation change drastically based on the rate of circulation, the species being grown, and the changing density of the culture.

The described embodiments may be combined to meet the needs of the specific culture or species of algae grown. The various illustrated embodiments of the fluid-light unit 206 may be modified to comply with different sizes and shapes of bioreactors, raceways, ponds, or other growth environments.

Figure 15:
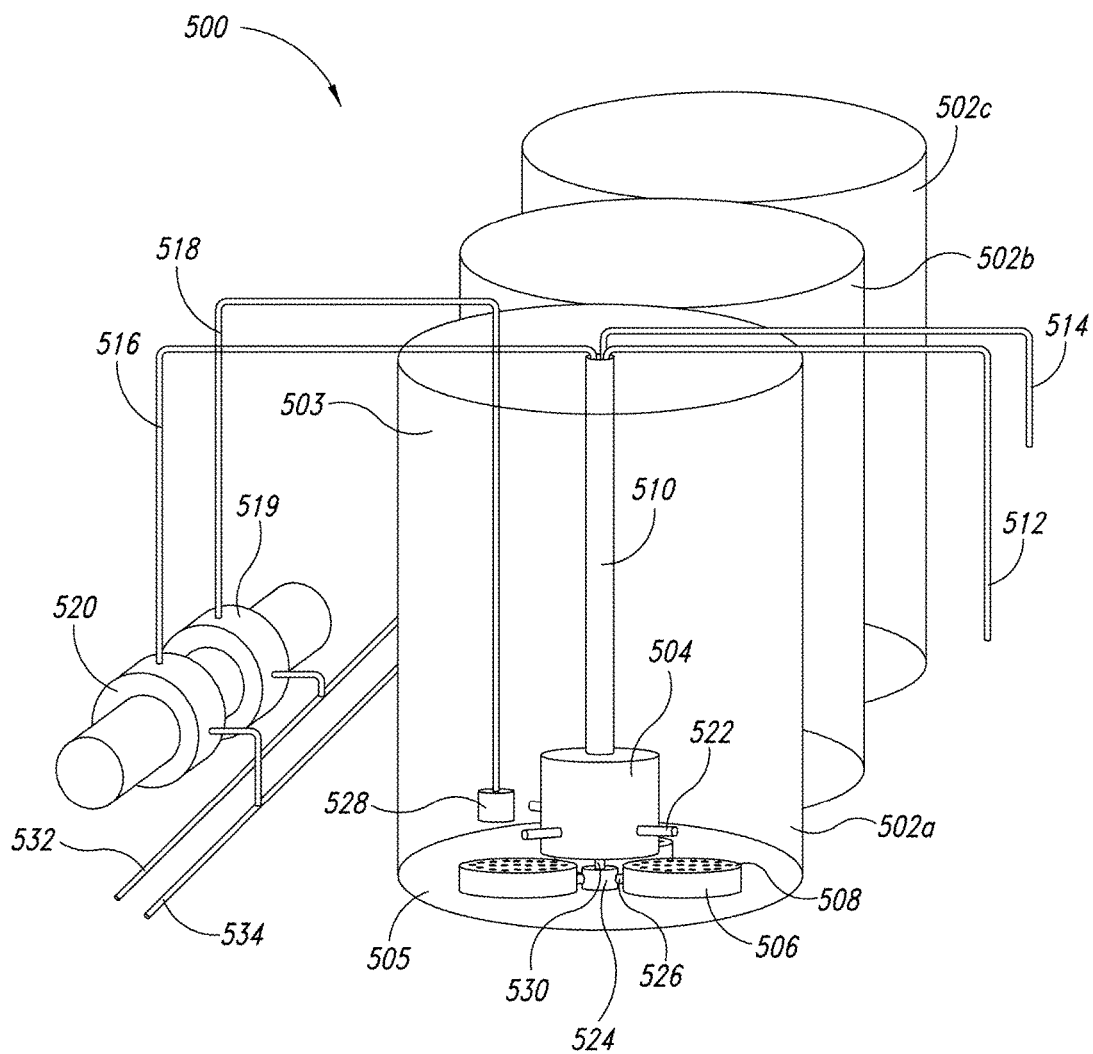
FIG. 15 is a production facility for providing light to a culture in accordance with an alternative embodiment of the present disclosure.

FIG. 15 illustrates a production facility 500 having a plurality of bioreactors 502a, 502b, and 502c configured to employ an embodiment of the present disclosure. The bioreactors 502 may be any size or shape based on the capacity of the production facility 500 and the culture being grown. Each bioreactor 502 provides a production space 503 adapted to contain the culture medium and to efficiently distribute photonic energy through the culture medium in the production space 203.

Three fluid-light units 506 are located on a bottom surface 505 of each bioreactor 502 and may be include any of the features described above with respect of the fluid-light units 206 of FIGS. 2-7A and 9-13. More particularly, each fluid-light unit 506 includes a photonic energy source (not shown)

that is separated from the culture medium in the production space 503 by an interface 508. The separation of the photonic energy source from the culture medium prevents biofilming.

An air-lift unit 504 is centered on a central axis of each bioreactor 502 and positioned above the fluid-light units 506. A hollow tube 510 attaches to the air-lift unit 504 to provide control circuitry and/or the energy transfer medium to the fluid-light units 506 and the air-lift unit 504. A first pipe 512 may provide filtered air while a second pipe 514 may provide nutrient gas to the air-lift unit 504 and to the fluid-light units 506. A third pipe 516 may provide a nutrient fluid to the fluid-light units 506. Other pipes may be incorporated into the production facility 500 to couple an external process controller (not shown) to the fluid-light units 506 and the air-lift unit 504.

The air-lift unit 504 may have a manifold 522 extending from a lower portion of the air-lift unit 504 and positioned overlying each fluid-light unit 506. The manifold 522 may have a plurality of holes drilled into a top surface that release filtered air, nutrient gas, or other fluid provided by the pipes 512 and 514. This arrangement is intended to ensure that the nutrients are fully and rapidly mixed into the culture medium. As the air or nutrient gas is released into the culture medium bubbles form and travel away from the fluid-light units 506. The air-lift bubbles help distribute the photonic energy coupled into the culture medium by the fluid-light units 506.

A connector 530 extends from the air-lift unit 504 to a device 524 that distributes the energy transfer medium to the fluid-light units 506 and may distribute the control circuitry to the photonic energy sources within the fluid-light units 506. The fluid-light units 506 attach to the distribution device 524 through another connector 526.

A pair of synchronized peristaltic pumps, in this case a harvest pump 519 and a nutrient pump 520, introduce nutrients and harvest the culture at equal volumes to maintain consistent volume and bio-mass density. The pumps 519, 520 may be controlled by sensors (not shown) to more precisely control the parameters of the culture in the bioreactor 502. Additional pipes 532 and 534 connect the pumps 519 and 520 with a nutrient supply or a harvest container (not shown). The pipes 532 and 534 may connect to other bioreactors 502b and 502c in the production facility 500. Each bioreactor 502 may have an individual set of the pumps 519 and 520, the associated pipes connecting the pumps 519 and 520 to the bioreactor 502, and the other components discussed with respect to bioreactor 502a. The features and size of the bioreactors 502 may be varied to meet the production needs of various facilities. This system may be manufactured as modular components for individualized production facilities as well as for the ease of maintenance. In addition, several systems may be run in parallel to meet industrial and environmental needs.

Figure 16:
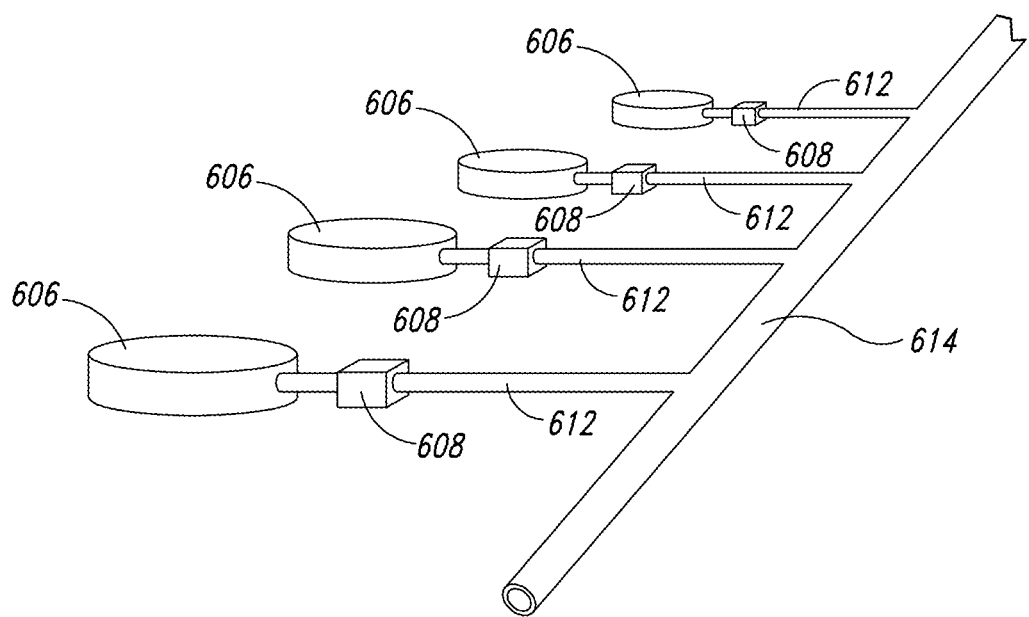
FIG. 16 is an isometric view of a plurality of fluid-light units for providing light to a plurality of cultures in accordance with yet another embodiment of the present disclosure.

FIG. 16 shows a group of fluid-light units 606 that are individually connected to a supply line 614 or central communication pipe via connection pipes 612. Each fluid-light unit 606 may be incorporated into a bioreactor or other growth environment, which is not shown for ease of illustration. The supply line 614 provides the energy-transfer medium to the connection pipes 612 and each fluid-light unit 606. A flow regulator 608 controls the flow of the energy-transfer medium into the fluid-light unit 606 to meet the needs of the culture medium. A sensor (not shown) may detect changes in parameters of the culture medium and transmit control signals to the flow regulator 608 to adjust the entry of the energy-transfer medium as needed.

Each fluid-light unit 606 has the dedicated flow regulator 608 to compensate for pressure differential along the supply line 614. Conditions of the local growth environment may influence flow properties, such as culture density, depth of the fluid-light unit, and temperature. Without flow regulators 608 fluid-light units 606 further away from a main source of the energy-transfer medium would see significantly lower flows than the fluid-light units 606 located closer to the main source.

The described embodiments are advantageous because of independence from the diurnal, seasonal, and geographic limitations of sunlight, the higher production rate from a fixed amount of equipment, and a smaller footprint. The embodiments experience a higher output rate due to 24-hour production. In addition, the $CO_2$ waste consumption ability of the algae or other autotrophic organisms can stay continuously on line.

Although efficient light delivery is particularly important for autotrophic organisms, the system described herein may be used to cultivate mixotrophic organisms. Additionally, the control and distribution of light can be used to limit the growth of undesirable competing organisms.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not to be limited by the disclosure.

The invention claimed is:

1. A device, comprising:
    a culture medium;
    a container configured to house the culture medium; and
    an assembly including a photonic device, the assembly is configured to generate a liquid energy transfer medium and deliver the liquid energy transfer medium between the culture medium and the photonic device to separate the photonic device from the culture medium, the assembly including one or more apertures sized and shaped to form one or more liquid replenishing lenses in response to the liquid energy transfer medium passing through the one or more apertures, the assembly including a fluid-light unit in the container configured to house the photonic device and to provide the liquid energy transfer medium, the fluid-light unit having the one or more apertures that are sized and shaped to form the one or more liquid replenishing lenses in response to the liquid energy transfer medium passing through the one or more apertures, wherein the photonic device is at least one from among a photoreceptor, a photoemitter, or a combination of the photoreceptor and the photoemitter, wherein the assembly further includes a pump coupled to the fluid-light unit and configured to continuously expose the photonic device to the liquid energy transfer medium, and wherein the assembly is configured to convey the photonic energy between the photonic device and the culture medium through the liquid energy transfer medium.

2. The device of claim 1 wherein the assembly that generates the liquid energy transfer medium is configured to continually replenish the liquid energy transfer medium.

3. The device of claim 1 wherein a quality of the liquid energy transfer medium is controlled by an immiscibility of the liquid energy transfer medium with respect to the culture medium.

4. The device of claim 1 wherein the liquid energy transfer medium is static for a period of time with respect to the photonic device.

5. The device of claim 4 wherein the photonic device is configured to receive photonic energy from the culture medium through the liquid energy transfer medium during the period of time the liquid energy transfer medium is static.

6. A device, comprising:
a culture medium;
a container configured to house the culture medium;
a photonic device structured to provide photonic energy, the photonic device is at least one from among a photoreceptor, a photoemitter, or a combination of the photoreceptor and the photoemitter; and
a generator including said photonic device, the generator configured to generate one or more liquid replenishing lenses and to deliver the one or more liquid replenishing lenses between the culture medium and the photonic device, the one or more liquid replenishing lenses configured to transmit photonic energy between the photonic device and the culture medium, the generator including an assembly configured to generate a liquid energy transfer medium and delivers the liquid energy transfer medium between the culture medium and the photonic device to separate the photonic device from the culture medium and to convey photonic energy between the photonic device and the culture medium, the assembly including a housing arranged in the container, the housing having an interface member that includes one or more apertures sized and shaped to form the one or more liquid replenishing lenses in response to the liquid energy transfer medium passing through the one or more apertures, the one or more liquid replenishing lenses structured to reflect and refract photonic energy at the time the one or more liquid replenishing lenses are in the one or more apertures and as the photonic energy travels through the one or more liquid replenishing lenses from the photonic device and into the culture medium, and wherein the assembly further includes a pump coupled to the housing and configured to continuously expose the photonic device to the liquid energy transfer medium.

7. The device of claim 6 wherein the photonic device is configured to be located a distance from the culture medium with the one or more liquid replenishing lenses forming a boundary between the photonic device and the culture medium.

8. The device of claim 6 wherein the photonic device is configured to receive photonic energy from the culture medium.

* * * * *